(12) United States Patent
Yamada et al.

(10) Patent No.: US 11,815,778 B2
(45) Date of Patent: Nov. 14, 2023

(54) ORGANIC COMPOUND AND ELECTROCHROMIC ELEMENT

(71) Applicant: CANON KABUSHIKI KAISHA, Tokyo (JP)

(72) Inventors: Kenji Yamada, Kanagawa (JP); Satoshi Igawa, Kanagawa (JP); Kazuho Saeki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 485 days.

(21) Appl. No.: 17/121,472

(22) Filed: Dec. 14, 2020

(65) Prior Publication Data

US 2021/0191217 A1 Jun. 24, 2021

(30) Foreign Application Priority Data

Dec. 18, 2019 (JP) .................................. 2019-228157
Jul. 22, 2020 (JP) .................................. 2020-124961

(51) Int. Cl.
*G02F 1/1516* (2019.01)
*C07D 471/04* (2006.01)
*G02F 1/155* (2006.01)
*C09K 9/02* (2006.01)

(52) U.S. Cl.
CPC ......... *G02F 1/1516* (2019.01); *C07D 471/04* (2013.01); *C09K 9/02* (2013.01); *G02F 1/155* (2013.01); *G02F 2203/01* (2013.01); *G02F 2203/02* (2013.01)

(58) Field of Classification Search
CPC ................................ C07D 471/04; C09K 9/02
See application file for complete search history.

(56) References Cited

U.S. PATENT DOCUMENTS

| 9,701,671 | B2* | 7/2017 | Igawa | .................. G02F 1/163 |
| 10,907,091 | B2* | 2/2021 | Igawa | .................. G03B 11/00 |
| 11,442,324 | B2* | 9/2022 | Kubo | .................. G02F 1/153 |
| 11,591,513 | B2* | 2/2023 | Igawa | .................. E06B 9/24 |
| 2019/0002758 | A1 | 1/2019 | Igawa et al. | |
| 2021/0109415 | A1* | 4/2021 | Igawa | .................. G02F 1/15 |

FOREIGN PATENT DOCUMENTS

| CN | 108779113 A | 11/2018 |
| EP | 3521398 A1 | 8/2019 |
| JP | 2016155802 A | 9/2016 |

OTHER PUBLICATIONS

Shah; Polymers 2019, 11(11), 1839; https://doi.org/10.3390/polym11111839 (Year: 2019).*
European Patent Office, European Search Report in Application EP20214287 dated Apr. 13, 2021. (Year: 2021).*

\* cited by examiner

*Primary Examiner* — Daniel R Carcanague
(74) *Attorney, Agent, or Firm* — Canon U.S.A., Inc., IP Division

(57) ABSTRACT

An organic compound that absorbs light of a wavelength range from 450 nm to 580 nm in a reduction state and is colored and that is superior in high-temperature drive durability and that is expressed by the following formula [1].

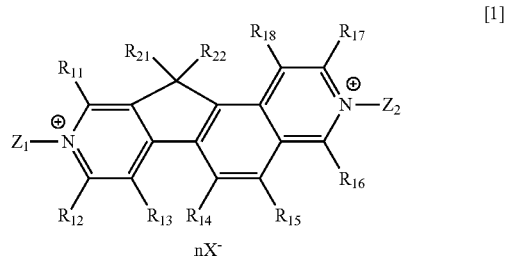

$Z_1$ and $Z_2$ each represent a substituent. $R_{11}$ to $R_{18}$ each represent a hydrogen atom or a substituent. $R_{12}$ and $R_{13}$ are optionally bound to each other to form a ring. $R_{21}$ and $R_{22}$ each represent a hydrogen atom or a substituent. $X^-$ represents an anion, and n is an integer greater than or equal to 1. When n is 2 or greater, two or more $X^-$s are the same or different from each other.

20 Claims, 6 Drawing Sheets

ORGANIC COMPOUND AND ELECTROCHROMIC ELEMENT

BACKGROUND OF THE INVENTION

Field of the Invention

The present disclosure relates to an organic compound having an electrochromic property and an electrochromic element having the organic compound.

Description of the Related Art

An electrochromic element is an element having a pair of electrodes and an electrochromic layer arranged between the pair of electrodes. The element adjusts the light amount of light passing through the electrochromic layer by applying a voltage between the pair of electrodes. That is, the electrochromic element can control light transmittance. Note that, in the present specification, "electrochromic" may be abbreviated as "EC".

As an EC material whose properties of optical absorption of substances (coloration state or light transmittance) are changed by an electrochemical oxidation-reduction reaction, various materials such as an inorganic material, an organic polymer material, and an organic low molecular material are known. A representative example of an organic low molecular EC material may be a viologen derivative (cathodic compound) that is colored by reduction, an oligothiophene derivative (anodic compound) that is colored by oxidation, or the like.

Conventionally, as application of the EC element, a dimming mirror of an automobile, an electronic paper, and the like are proposed. Such an EC element uses characteristics that various color tones can be displayed in accordance with selection of materials. That is, it is suggested that development of materials having various color tones may enable application to a wide range of uses. For example, when application to a full-color display or the like is intended, a material to be colored in cyan, magenta, and yellow is required. When application to a wider range of uses is intended, an organic EC material that enables various color design by designing molecules is attracted attention because an EC material having various absorption wavelengths at coloring is required.

To configure a device that absorbs light of a wide range of the visible light region by using an EC compound, various EC compounds are required for absorbing light having various wavelengths. A typical viologen derivative that is a representative example of a cathodic EC compound with an organic low molecule has an absorption range in a wavelength range near 400 nm and near 600 nm at reduction coloring. Thus, a cathodic EC compound exhibiting color absorption in a range other than such a wavelength range has been desired. Japanese Patent Application Laid-Open No. 2016-155802 discloses an EC compound having an absorption range in a range near 480 nm at reduction coloring.

For practical use of an EC element, high-temperature durability is necessary in accordance with a use of an applied device. In an organic low molecular EC compound, particularly a cathodic EC compound exhibiting absorption in a wavelength range from 450 nm to 580 nm at coloring, further improvement of high-temperature drive durability due to radical cation instability in a reduction state is desired.

SUMMARY OF THE INVENTION

The present disclosure has been made in view of the above disadvantage and intends to provide an organic compound that absorbs light in a wavelength range from 450 nm to 580 nm in a reduction state and is colored and that is superior in high-temperature drive durability.

The present disclosure provides an organic compound expressed by the following formula [1].

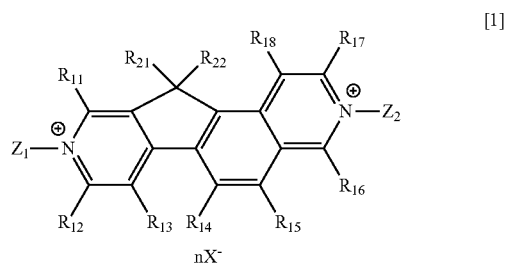

[1]

In formula [1], $Z_1$ and $Z_2$ are respectively, independently selected from an alkyl group optionally having a substituent, an aryl group optionally having a substituent, and an aralkyl group optionally having a substituent.

$R_{11}$ to $R_{18}$ are respectively, independently selected from a hydrogen atom, an alkyl group optionally having a substituent, an alkoxy group optionally having a substituent, an aryl group optionally having a substituent, a heterocyclic group optionally having a substituent, and a halogen atom. $R_{12}$ and $R_{13}$ optionally bound to each other to form a ring.

$R_{21}$ and $R_{22}$ are respectively, independently selected from a hydrogen atom, a hydroxyl group, an alkyl group optionally having a substituent, an alkoxy group optionally having a substituent, an aryl group optionally having a substituent, and an aralkyl group optionally having a substituent.

$X^-$ represents an anion, n is an integer greater than or equal to 1. When n is 2 or greater, two or more $X^-$s are the same or different from each other.

Further features of the present disclosure will become apparent from the following description of exemplary embodiments with reference to the attached drawings.

DESCRIPTION OF THE EMBODIMENTS

<<Organic Compound>>

Figure 1:
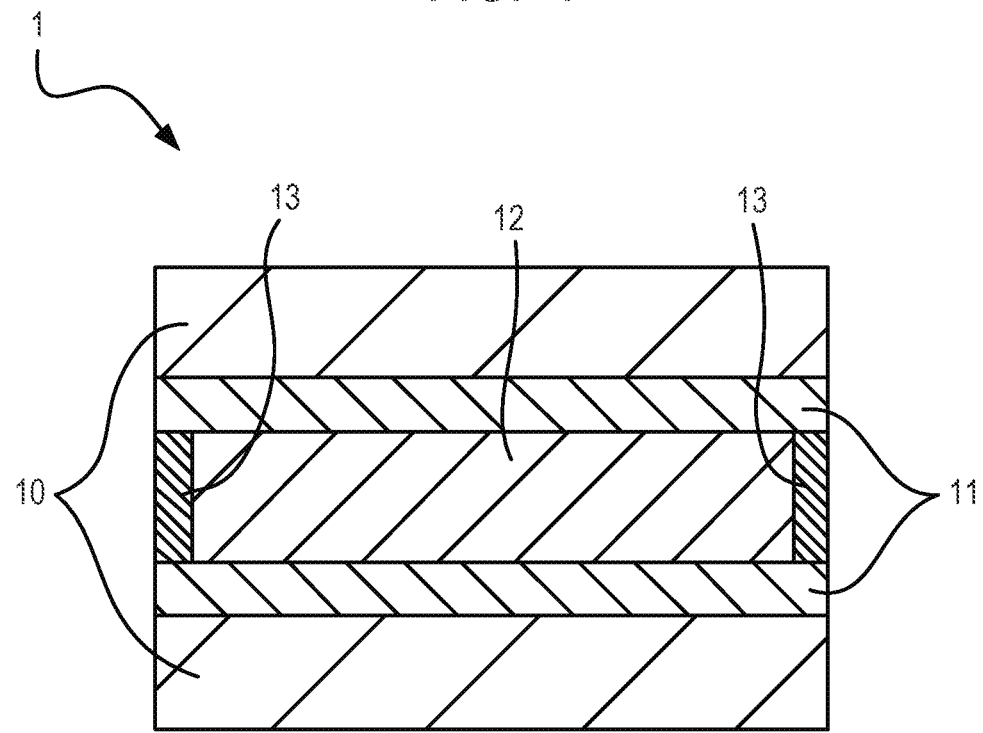
FIG. 1 is a sectional schematic diagram of an example of an EC element according to an embodiment.

An organic compound according to the present embodiment is expressed by the following general formula [1]. The organic compound according to the present embodiment has an EC property and can thus be called an EC compound.

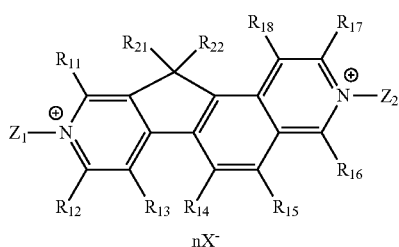

[1]

nX⁻

<$Z_1$ and $Z_2$>

The groups "$Z_1$" and "$Z_2$" are respectively, independently selected from an alkyl group that may have a substituent, an aryl group that may have a substituent, and an aralkyl group that may have a substituent. The groups "$Z_1$" and "$Z_2$" each are preferably an alkyl group that may have a substituent.

The alkyl group may be an alkyl group with 1-20 carbon atoms. The terminal of the alkyl group may be an adsorbing group or an acid ester thereof. With the adsorbing group, it is also possible to be immobilized on a porous electrode. A specific example of an adsorbing group or an acid ester thereof may be, for example, a carboxyl group and a carboxyl ester group, a sulfonic acid group and a sulfonic acid ester group, a phosphonic acid group and a phosphonic acid ester group, a trialkoxysilyl group, an acyl group, or the like. Further, to improve solubility in an organic solvent, the terminal of the alkyl group may have a polar group such as a hydroxy group or an amino group, or an ionic group such as an ammonium, a pyridinium, or a quinolinium. Further, the terminal of the alkyl group may be substituted with a halogen-substituted alkyl group such as a trifluoromethyl group in which hydrogen atoms are substituted with a halogen atom, an alkoxy group, an ester group, or a cyano group.

The aryl group may be, for example, a phenyl group, a biphenyl group, a tolyl group, a fluorenyl group, a naphthyl group, a fluoranthenyl group, an anthryl group, a phenanthryl group, a pyrenyl group, a perylenyl group, or the like. A phenyl group is preferable. The aryl group may have a halogen atom, an alkyl group with 1-8 carbon atoms, an alkoxy group with 1-4 carbon atoms, an aryl group, an aralkyl group, a hydroxy group, a substituted amino group, or a substituted silyl group as a substituent. The hydrogen atom in the alkyl group or the alkoxy group may be substituted with a halogen atom, and preferably a fluorine atom. Further, the terminal of the alkyl group or the alkoxy group may have an adsorbing group or the acid ester group thereof for adsorbing to the porous electrode and may have an ionic group for improving solubility in an organic solvent. Specific examples of the adsorbing group or acid ester group thereof, and the ionic group are the same as the examples in the case of the alkyl group.

The aralkyl group may be, for example, a benzyl group, a phenethyl group, or the like. The aralkyl group may have a substituent, and specifically may have an alkyl group with 1-8 carbon atoms, an alkoxy group with 1-8 carbon atoms, or an adsorbing group or the acid ester group thereof for adsorbing to the porous electrode. The hydrogen atom in the alkyl group or the alkoxy group may be substituted with a halogen atom, and preferably a fluorine atom. The terminal of the alkyl group or the alkoxy group may have an adsorbing group or the acid ester group thereof for adsorbing to the porous electrode and may have an ionic group for improving solubility in an organic solvent. Specific examples of the adsorbing group or acid ester group thereof, and the ionic group are the same as the examples in the case of the alkyl group.

<$R_{11}$ to $R_{18}$>

The groups $R_{11}$ to $R_{18}$ are respectively, independently selected from a hydrogen atom, an alkyl group that may have a substituent, an alkoxy group that may have a substituent, an aryl group that may have a substituent, a heterocyclic group that may have a substituent, and a halogen atom. All of $R_{11}$ to $R_{18}$ may be hydrogen atoms.

The alkyl group is preferably an alkyl group with 1-8 carbon atoms and may be linear, branched, or cyclic. Specifically, a methyl group, an ethyl group, a normal propyl group, an isopropyl group, a normal butyl group, a tertiary butyl group, an octyl group, a cyclohexyl group, a trifluoromethyl group, or the like may be used. Further, the hydrogen atom may be substituted with a fluorine atom. Further, the carbon atoms in the alkyl group may be substituted with an ester group, a cyano group, or an oxygen atom.

The alkoxy group may be linear, branched, or cyclic. The alkoxy group preferably has 1-8 carbon atoms. Specifically, for example, a methoxy group, an ethoxy group, an isopropoxy group, an n-butoxy group, a tert-butoxy group, an ethylhexyloxy group, an octyloxy group, a benzyloxy group, a trifluoromethoxy group, or the like may be used. Among others, a methoxy group, an ethoxy group, or an isopropoxy group is particularly preferable. The hydrogen atom in the alkoxy group may be substituted with a halogen atom.

The aryl group may be a phenyl group, a biphenyl group, a tolyl group, a fluorenyl group, a naphthyl group, a fluoranthenyl group, an anthryl group, a phenanthryl group, a pyrenyl group, a perylenyl group, or the like, for example. A phenyl group is preferable.

The heterocyclic group may be, for example, a pyridyl group, a thienyl group, an oxazolyl group, an oxadiazolyl group, a thiazolyl group, a thiadiazolyl group, an indolyl group, or the like. A pyridyl group is preferable.

The aryl group and the heterocyclic group may have a halogen atom, an alkyl group with 1-6 carbon atoms, an alkoxy group with 1-4 carbon atoms, an aryl group, an aralkyl group, a hydroxy group, a substituted amino group, or a substituted silyl group as a substituent. The hydrogen atom in the alkyl group or the alkoxy group may be substituted with a halogen atom, and preferably a fluorine atom.

The halogen atom may be fluorine, chlorine, bromine, iodine, or the like.

For example, another substituent that the alkyl group, the alkoxy group, the aryl group, and the heterocyclic group may have may be, for example, an amino group, for example, a substituted amino group such as a methylamino group, a thiol group, or the like but is not limited thereto.

$R_{12}$ and $R_{13}$ may be bound to each other to form a ring. $R_{12}$ and $R_{13}$ being bound to each other to form a ring means that the ring formed of bound $R_{12}$ and $R_{13}$ and a pyridine ring in which $R_{12}$ and $R_{13}$ are bound form a condensed ring. The ring formed of the bound $R_{12}$ and $R_{13}$ may be an aromatic ring with 5-18 carbon atoms, or an alicyclic structure with 5-18 carbon atoms. Further, the ring formed of the $R_{12}$ and $R_{13}$ bound to each other may be a condensed ring. More specifically, a benzene ring, a naphthalene ring, a pyridine ring, a thiophene ring, a pyrrole ring, a cyclohexane ring, a cyclopentane ring, or the like may be used. A benzene ring is preferable.

<$R_{21}$ and $R_{22}$>

The groups $R_{21}$ and $R_{22}$ are respectively, independently selected from a hydrogen atom, a hydroxyl group, an alkyl group that may have a substituent, an alkoxy group that may have a substituent, an aryl group that may have a substituent, and an aralkyl group that may have a substituent.

The alkyl group is preferably an alkyl group with 1-8 carbon atoms and may be linear, branched, or cyclic. Specifically, a methyl group, an ethyl group, a normal propyl group, an isopropyl group, a normal butyl group, a tertiary butyl group, an octyl group, a cyclohexyl group, a trifluoromethyl group, or the like may be used. Further, the hydrogen atom may be substituted with a fluorine atom. Further, the carbon atom in the alkyl group may be substituted with an ester group or a cyano group.

The alkoxy group may be linear, branched, or cyclic. The alkoxy group preferably has 1 to 8 carbon atoms. Specifically, for example, a methoxy group, an ethoxy group, an isopropoxy group, an n-butoxy group, a tert-butoxy group, an ethylhexyloxy group, an octyloxy group, a benzyloxy group, a trifluoromethoxy group, or the like may be used. Among others, a methoxy group, an ethoxy group, or an isopropoxy group is particularly preferable. The hydrogen atom in the alkoxy group may be substituted with a halogen atom.

The aryl group may be, for example, a phenyl group, a biphenyl group, a tolyl group, a fluorenyl group, a naphthyl group, a fluoranthenyl group, an anthryl group, a phenanthryl group, a pyrenyl group, a perylenyl group, or the like. A phenyl group is preferable. The aryl group may have a halogen atom, an alkyl group with 1-6 carbon atoms, an alkoxy group with 1-4 carbon atoms, an aryl group, an aralkyl group, a hydroxy group, a substituted amino group, or a substituted silyl group as a substituent. The hydrogen atom in the alkyl group or the alkoxy group may be substituted with a halogen atom, and preferably a fluorine atom.

The aralkyl group may be, for example, a benzyl group, a phenethyl group, or the like. The aralkyl group may have a substituent, and specifically may have an alkyl group with 1-8 carbon atoms, or an alkoxy group with 1-8 carbon atoms. The hydrogen atom in the alkyl group or the alkoxy group may be substituted with a halogen atom, and preferably a fluorine atom.

<$X^-$, n>

The symbol "$X^-$" represents an anion, and preferably a monovalent anion, and the symbol "n" is an integer of 1 or greater, and preferably an integer of 2 or greater. An anion expressed by $X^-$ is selected from an anion such as $PF_6^-$, $ClO_4^-$, $BF_4^-$, $AsF_6^-$, $SbF_6^-$, $CF_3SO_3^-$, or $(CF_3SO_2)_2N^-$ or a halogen anion such as $Br^-$, $Cl^-$, or $I^-$. Any one of $PF_6^-$, $ClO_4^-$, $BF_4^-$, $CF_3SO_3^-$, and $(CF_3SO_2)_2N^-$ is preferable. When n is 2 or greater, $X^-$s may be the same as or different from each other.

The method for manufacturing the organic compound according to the present embodiment is not particularly limited, and the organic compound can be manufactured by the method described below, for example.

When $Z_1$ and $Z_2$ each are an alkyl group or an aralkyl group, the organic compound expressed in the following general formula [2], and an alkyl halide compound or an aralkyl halide compound are reacted in a predetermined solvent. Then, by anion exchange reaction with a salt containing a desired anion in a predetermined solvent, a compound in which $Z_1$ and $Z_2$ are an alkyl group or an aralkyl group, respectively, can be obtained.

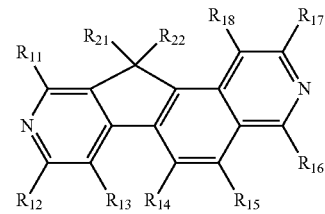

[2]

When $Z_1$ and $Z_2$ each are an aryl group, the organic compound expressed by the general formula [2] and 2,4-dinitrophenyl halide are reacted to synthesize an intermediate in which $Z_1$ and $Z_2$ each are a 2,4-dinitrophenyl group. Then, by causing the intermediate to react with arylamine and be subjected to an anion exchange reaction with a salt containing an anion in a predetermined solvent, it is possible to obtain a compound in which $Z_1$ and $Z_2$ are an aryl group. Further, by selecting a solvent and a reaction temperature, it is also possible to react only the imine on one side. By repeating the reaction, it is also possible to introduce substituents that are different from each other into the two imines.

The manufacturing method of the organic compound of the above general formula [2] is not particularly limited, and the organic compound can be manufactured according to the manufacturing method described below as an example, for example.

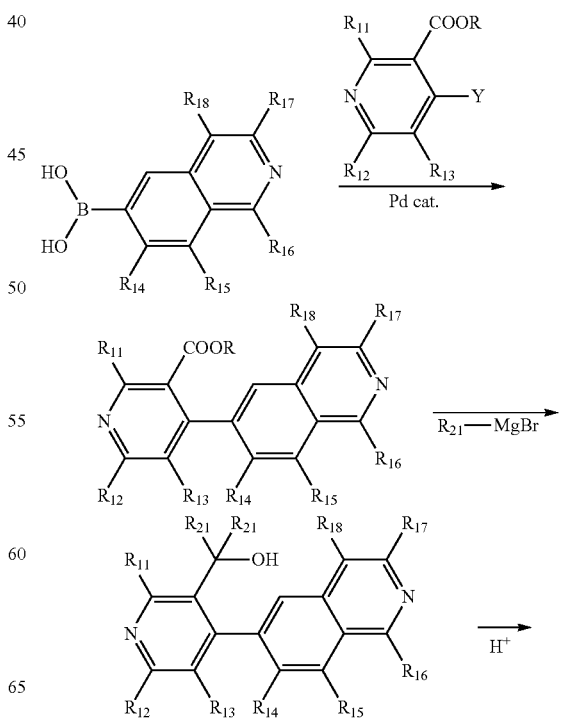

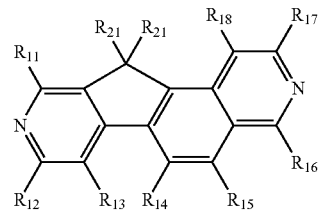

In the above formula, the group "Y" is a halogen atom, and the group "R" is an alkyl group. With a combination of a halogenated compound of pyridine having an ester group at the 3-position and 6-isoquinoline boronic acid or a boronic acid ester compound, a precursor can be synthesized by a known Pd-catalyzed coupling reaction. The combination of halogen compound and boronic acid or boronic acid ester compound may be opposite to the above. The organic compound expressed by the general formula [2] can be synthesized by reacting such a coupling compound with a Grignard reagent and further performing a cyclization reaction with an acid.

A specific structural formula of the compounds according to the present disclosure will be illustrated below as an example. Note that the compound according to the present disclosure is not limited thereto.

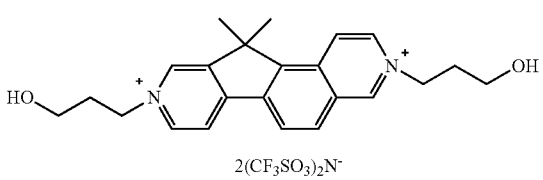

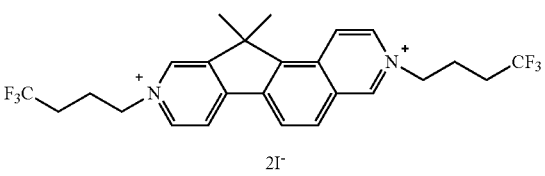

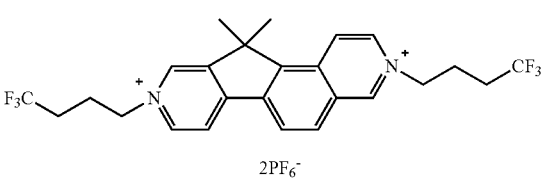

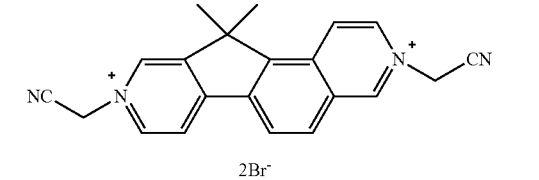

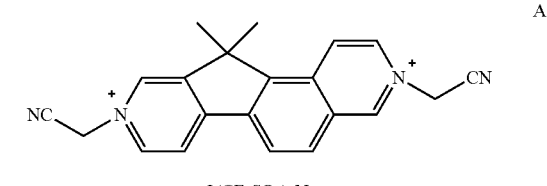

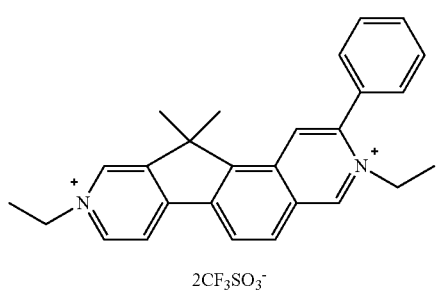

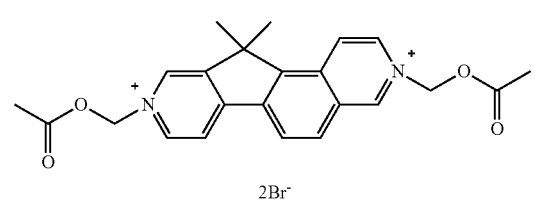

-continued
A-12
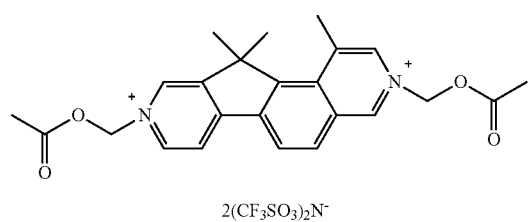
2(CF₃SO₃)₂N⁻
A-13
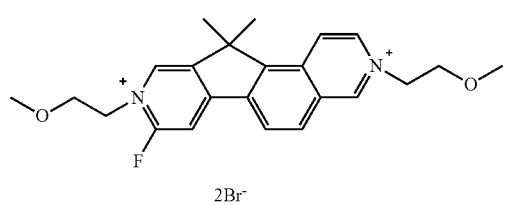
2Br⁻
A-14
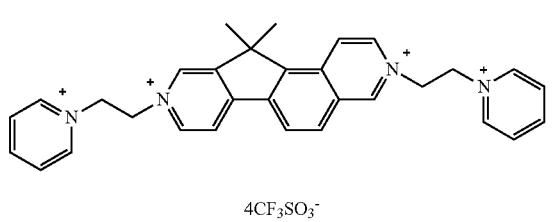
4CF₃SO₃⁻
A-15
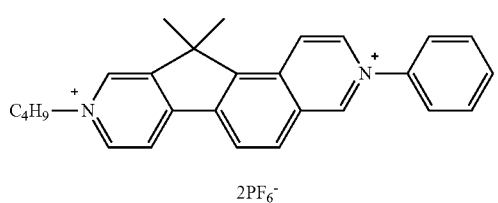
2PF₆⁻
A-16
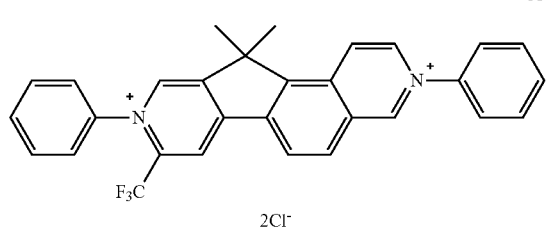
2Cl⁻
A-17
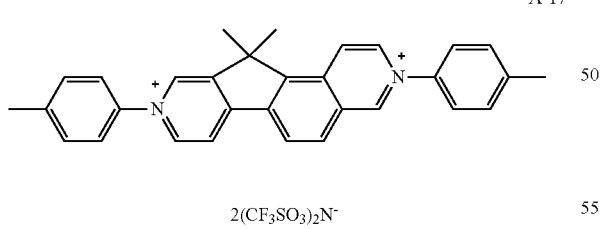
2(CF₃SO₃)₂N⁻
A-18
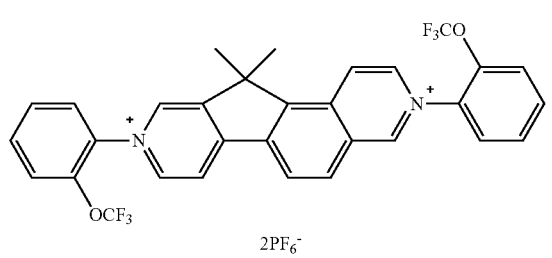
2PF₆⁻
-continued
A-19
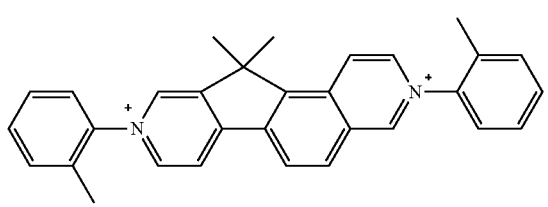
2Br⁻
A-20
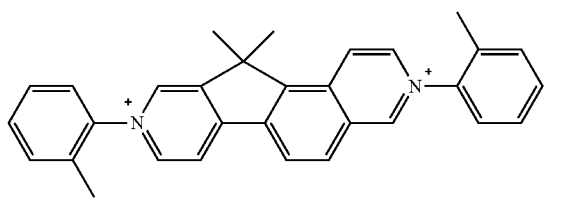
2PF₆⁻
A-21
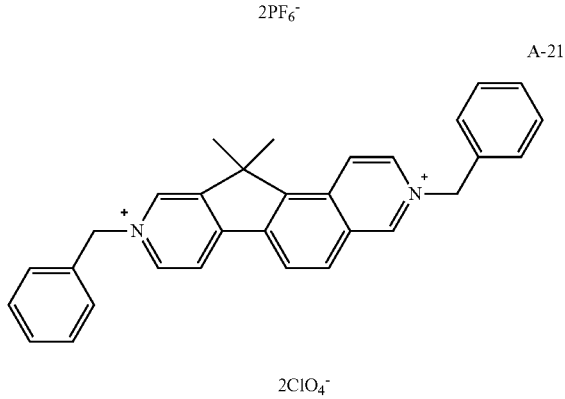
2ClO₄⁻
A-22
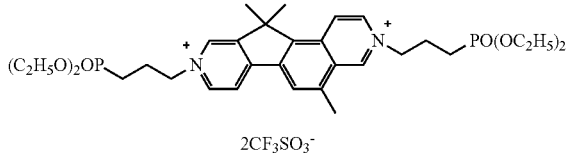
2CF₃SO₃⁻
A-23
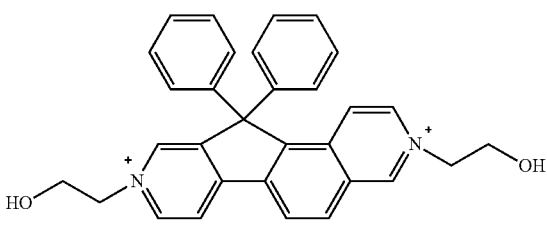
2BF₄⁻
A-24
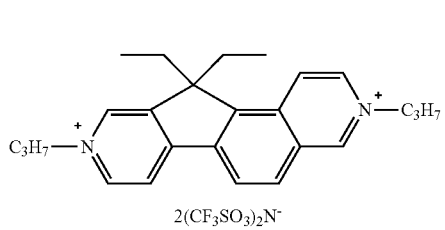
2(CF₃SO₃)₂N⁻

A-25
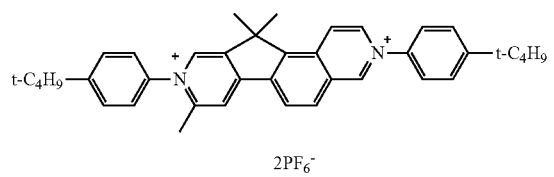
2PF₆⁻
B-1
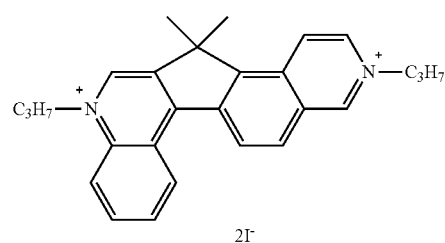
2I⁻
B-2
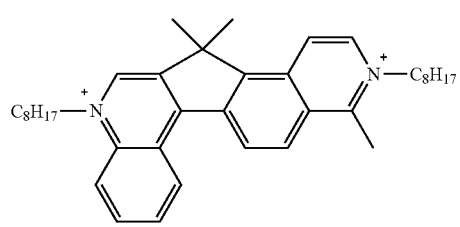
2(CF₃SO₃)₂N⁻
B-3
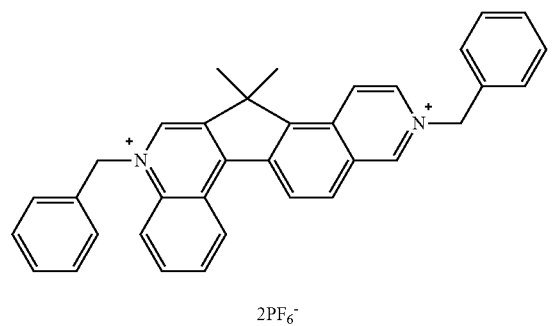
2PF₆⁻
B-4
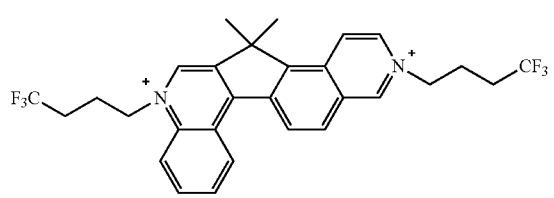
2I⁻
B-5
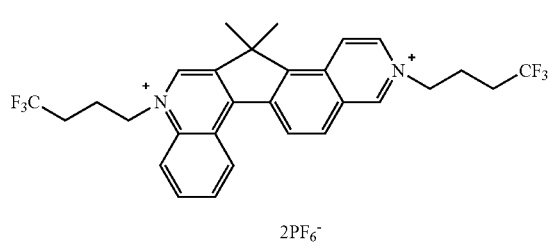
2PF₆⁻
B-6
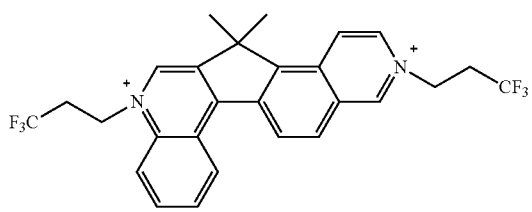
2CF₃SO₃⁻
B-7
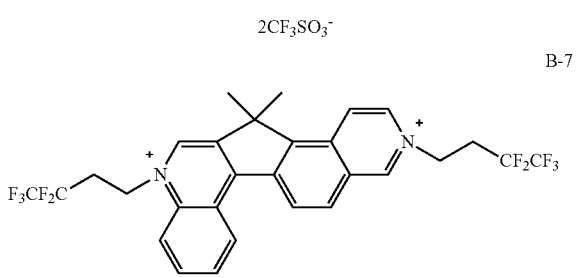
2PF₆⁻
B-8
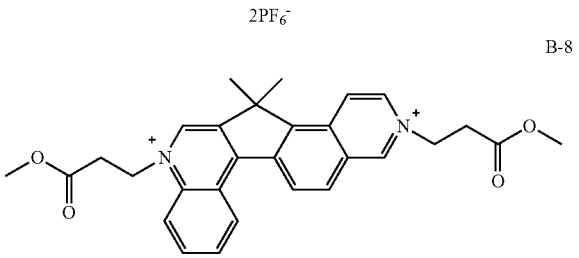
2Br⁻
B-9
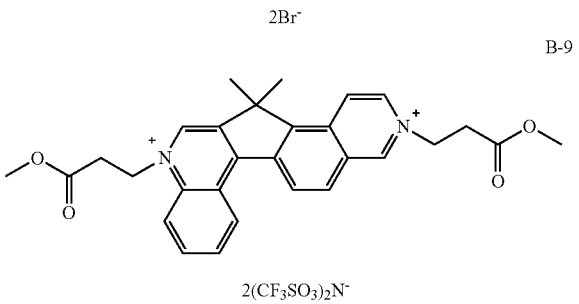
2(CF₃SO₃)₂N⁻
B-10
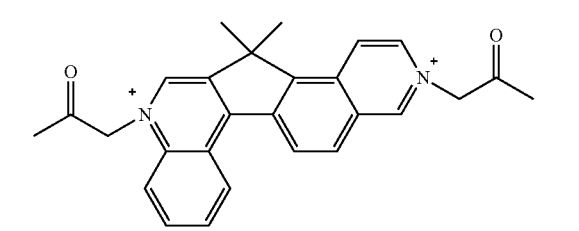
2ClO₄⁻
B-11
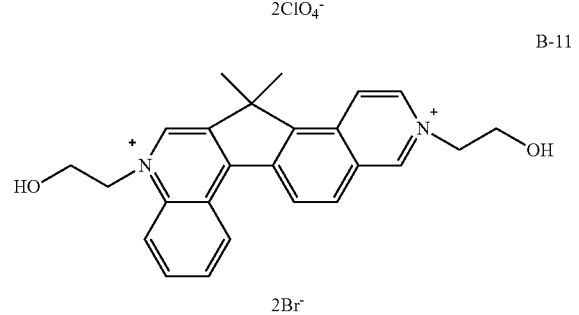
2Br⁻

-continued

B-12

2CF$_3$SO$_3^-$

B-13

2BF$_4^-$

B-14

4Br$^-$

B-15

2PF$_6^-$

B-16

2(CF$_3$SO$_3$)$_2$N$^-$

B-17

4I$^-$

-continued

B-18

4(CF$_3$SO$_3$)$_2$N$^-$

B-19

2Br$^-$

B-20

2PF$_6^-$

B-21

2BF$_4^-$

B-22

2(CF$_3$SO$_3$)$_2$N$^-$

B-23

2Br$^-$

-continued
B-24
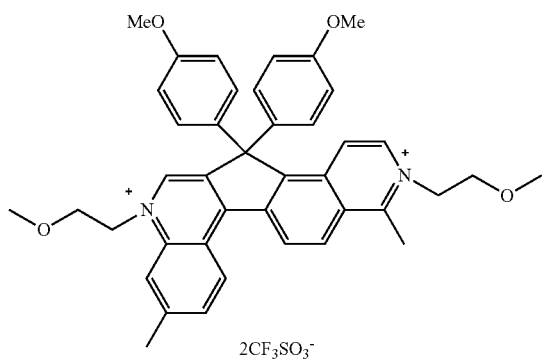
2CF₃SO₃⁻
B-25
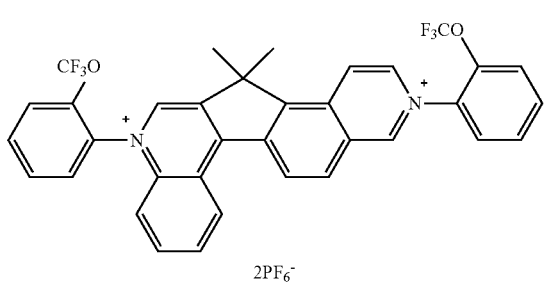
2PF₆⁻
B-26
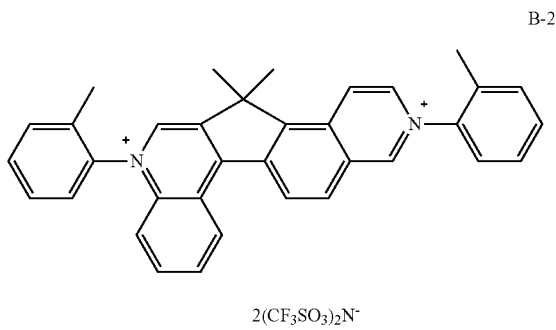
2(CF₃SO₃)₂N⁻
B-27
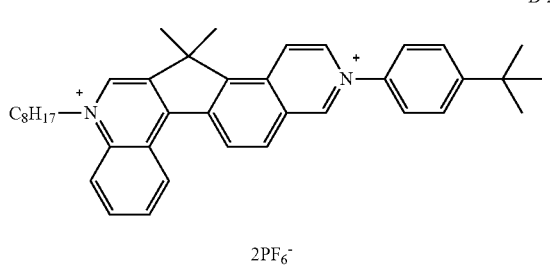
2PF₆⁻
B-28
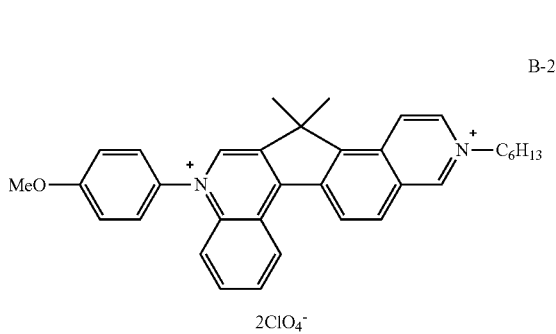
2ClO₄⁻
-continued
B-29
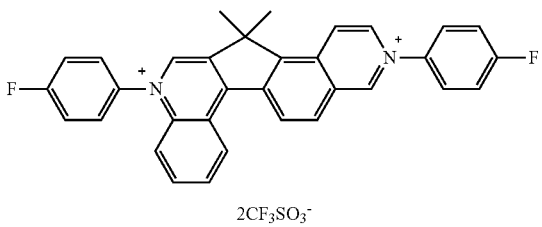
2CF₃SO₃⁻
B-30
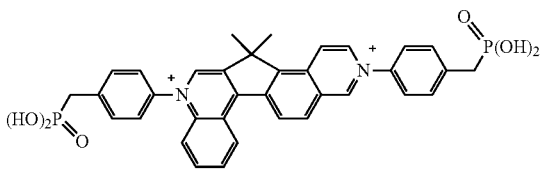
2Cl⁻
B-31
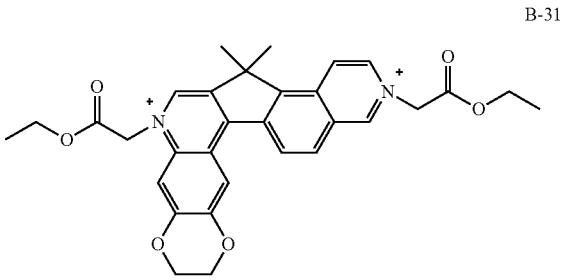
2PF₆⁻
B-32
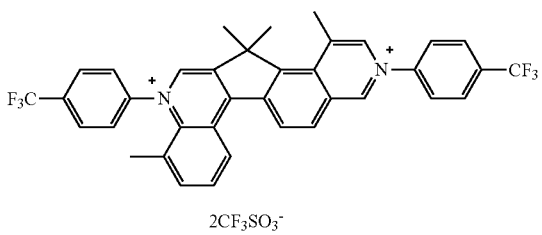
2CF₃SO₃⁻
B-33
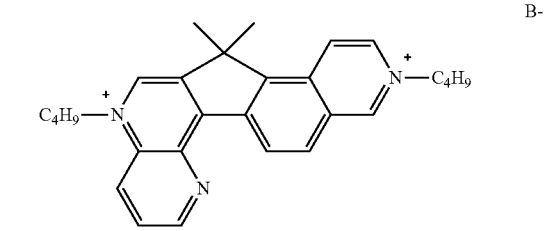
2PF₆⁻
B-34
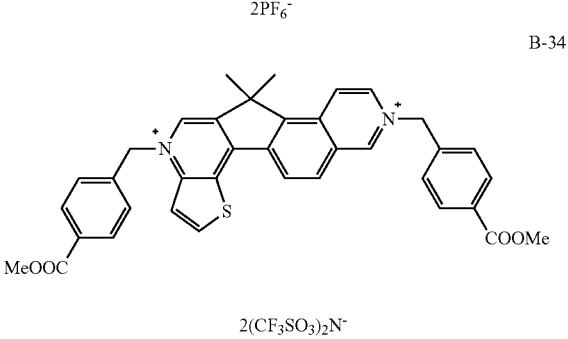
2(CF₃SO₃)₂N⁻

-continued

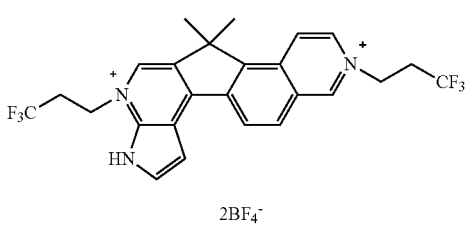

B-35

2BF$_4^-$

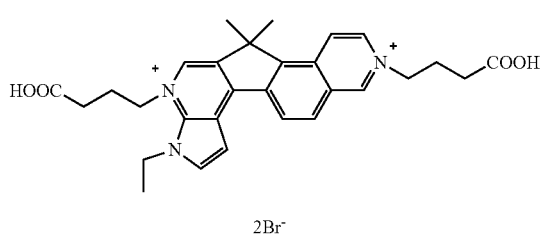

B-36

2Br$^-$

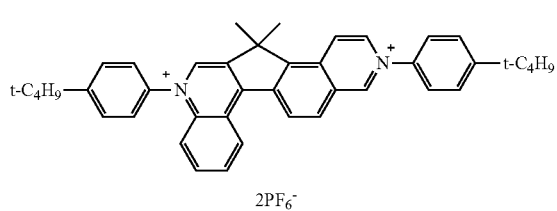

B-37

2PF$_6^-$

The compounds illustrated in A-group out of exemplified compounds are examples of a compound in which $R_{12}$ and $R_{13}$ in the general formula [1] each are a hydrogen atom or have a pyridine ring substituted with an alkyl group or a halogen atom. On the other hand, the compounds illustrated in B-group are examples of a compound of the structure in which $R_{12}$ and $R_{13}$ in the general formula [1] are bound to each other to form a ring.

Next, the characteristics based on the structure of the organic compound according to the present disclosure will be described. The organic compound expressed by the general formula [1] is a cathodic EC compound colored in a reduction state. That is, the organic compound expressed by the general formula [1] is a compound whose optical absorption properties (coloration state and light transmittance) are changed due to reversible progress of the electrochemical oxidation-reduction reaction. The organic compound expressed by the general formula [1] has an absorption peak in a wavelength range from 450 nm to 580 nm in a reduction state.

A viologen derivative that is a representative example of an organic cathodic EC compound exhibits absorption in a wavelength range near 400 nm and near 600 nm at reduction coloring. A general viologen derivative is expressed in a chemical structure of 4,4'-bipyridinium salt consisting of two pyridine rings. One scheme for causing the absorption wavelength range at coloring to be a longer wavelength range than that of a typical viologen derivative may be a molecular design scheme for extended conjugated structure of a bipyridinium salt backbone that is an EC site as disclosed in Japanese Patent Application Laid-Open No. 2016-155802. That is, a compound forming the EC site with two aromatic rings of a pyridine ring and an isoquinoline ring exhibits absorption in a range near 500 nm at reduction coloring. Such absorption is light absorption in accordance with the electronic energy transition corresponding to reduction coloring absorption near 400 nm of a general viologen derivative. However, further improvement in the stability of the compound at high temperature is desired. This is because a radical cation is formed at the EC site during reduction coloring and the instability thereof causes the need for the improvement.

Accordingly, in the organic compound according to the present disclosure, the flatness as a molecule is enhanced by introducing a crosslinked structure between a pyridine ring and an isoquinoline ring, and thereby the stability as a radical cation is enhanced. As the flatness of the molecule increases, the degree of radical delocalization also increases, and radical-caused side reactions such as recombination between radicals, hydrogen abstraction, and reaction with oxygen can be reduced. Therefore, it can be considered that superior durability can be exhibited even when an EC element including the organic compound according to the present disclosure is driven at a high temperature.

Since the organic compound according to the present disclosure has an absorption peak in the range near 500 nm at coloring and has high-temperature stability, the organic compound can be used for an EC element that is superior in high-temperature drive durability and an optical filter, a lens unit, an imaging apparatus, and the like using the same.

<<EC Element>>

The organic compound according to the present disclosure can be used as an EC layer of the electrochromic element. The EC element according to the present embodiment will be described below with reference to the drawings.

An EC element 1 of FIG. 1 is an EC element having a pair of transparent electrodes 11 and an EC layer 12 having an electrolyte arranged between the pair of electrodes 11 and the organic compound according to the present disclosure. In the pair of transparent electrodes 11, the distance between the electrodes is constant due to a seal member 13. In the EC element, the pair of transparent electrodes 11 is arranged between a pair of transparent substrates 10.

The EC layer 12 has the organic compound according to the present disclosure. The EC layer 12 may have a layer formed of an EC compound and a layer formed of an electrolyte. Further, the EC layer 12 may be provided as a solution layer having an EC compound and an electrolyte. The EC element according to the present embodiment is preferably an EC element whose EC layer 12 is a solution layer.

Next, members forming the EC element according to the present embodiment will be described. The electrolyte is not limited as long as it is an ionic dissociative salt and has good solubility in solvents and high compatibility in solid electrolytes. Among others, an electrolyte having electron donation is preferable. Such an electrolyte can be also referred to as a supporting electrolyte. The electrolyte may be, for example, an inorganic ion salt such as various alkali metal salts or alkaline earth metal salts, a quaternary ammonium salt or a cyclic quaternary ammonium salt, or the like. Specifically, an alkali metal salt of Li, Na, or K such as LiClO$_4$, LiSCN, LiBF$_4$, LiAsF$_6$, LiCF$_3$SO$_3$, LiPF$_6$, LiI, NaI, NaSCN, NaClO$_4$, NaBF$_4$, NaAsF$_6$, KSCN, or KCl, a quaternary ammonium salt and a cyclic quaternary ammonium salt such as (CH$_3$)$_4$NBF$_4$, (C$_2$H$_5$)$_4$NBF$_4$, (n-C$_4$H$_9$)$_4$NBF$_4$, (n-C$_4$H$_9$)$_4$NPF$_6$, (C$_2$H$_5$)$_4$NBr, (C$_2$H$_5$)$_4$NC$_{104}$, or (n-C$_4$H$_9$)$_4$NClO$_4$, or the like may be used.

A solvent that dissolves the EC compound and the electrolyte is not particularly limited as long as the solvent can dissolve the EC compound and the electrolyte, and in particular, a solvent having polarity is preferable. Specifically, water or an organic polar solvent such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionnitrile, 3-methoxypropionnitrile, benzonitrile, dimethyl acetamide, methylpyrrolidinone, dioxolane, or the like may be used. These solvents may be used alone, or two or more types of these solvents may be used in combination.

Moreover, the EC layer 12 can further contain a polymer or a gelling agent to form a high-viscous layer, a gelling layer, or the like. Such a polymer or a gelling agent may also be referred to as a thickener. When the EC layer 12 has a thickener, and the viscosity of the EC layer 12 is increased, an organic compound is less likely to form aggregates, and the temperature dependence of the absorption spectrum can be reduced. Accordingly, the EC layer 12 preferably has a thickener. When the mass of the EC layer 12 is 100 wt %, the thickener may have a mass ratio that is less than or equal to 20 wt %. Preferably, the mass ratio is greater than or equal to 1 wt % and less than or equal to 15 wt %, and more preferably greater than or equal to 5 wt % and less than or equal to 10 wt %.

The viscosity of the EC layer 12 may be 10 cP to 5,000 cP and may be 50 cP to 1,000 cP. The viscosity of the EC layer 12 may be less than or equal to 150 cP, preferably less than or equal to 100 cP, and more preferably less than or equal to 65 cP. Further, the viscosity of the EC layer 12 may be greater than or equal to 20 cP, and preferably greater than or equal to 50 cP.

A polymer that is a thickener is not particularly limited and may be, for example, polyacrylonitrile, carboxymethyl cellulose, polyvinyl chloride, polyethylene oxide, polypropylene oxide, polyurethane, polyacrylate, polymethacrylate, polyamide, polyacrylamide, polyester, Nafion (registered trademark), or the like.

Next, the transparent substrate 10 and the transparent electrode 11 will be described. For example, as the transparent substrate 10, a colorless or colored transparent resin may be used in addition that a colorless or colored glass, a tempered glass, or the like are used. Note that the term "transparent" in the present embodiment means that visible light transmittance is greater than or equal to 70%. Specifically, polyethylene terephthalate, polyethylene naphthalate, polynorbornene, polyamide, polysulfone, polyethersulfone, polyetheretherketone, polyphenylene sulfide, polycarbonate, polyimide, polymethylmethacrylate, or the like may be used.

The material for the transparent electrode 11 may be, for example, a metal or a metal oxide such as indium tin oxide alloy (ITO), fluorine-doped tin oxide (FTO), tin oxide (NESA), indium zinc oxide (IZO), silver oxide, vanadium oxide, molybdenum oxide, gold, silver, platinum, copper, indium, or chromium, a silicon-based material such as polycrystalline silicon or amorphous silicon, a carbon material such as carbon black, graphite, or glassy carbon, or the like. Further, a conductive polymer having improved conductivity with doping treatment or the like, for example, polyaniline, polypyrrole, polythiophene, poly acetylene, poly(p-phenylene), a complex of polyethylenedioxythiophene (PEDOT) and polystyrene sulfonate, or the like may also be suitably used.

To hold the EC layer 12 between the pair of transparent electrodes 11 and maintain the distance between both electrodes, the seal member 13 is preferably used. The seal member 13 may include a spacer material or the like to have a function of maintaining the distance between electrodes. The seal member 13 is arranged between the pair of transparent electrodes 11 and provides a space for accommodating the EC layer 12. The seal member 13 is preferably formed of a material that is chemically stable, is less likely to allow a gas and a liquid to permeate, and does not inhibit an oxidation-reduction reaction of an EC compound. Specifically, an inorganic material such as glass frit, a thermosetting or photocurable material such as an epoxy-based or acrylic-based resin, polyimide, polytetrafluoroethylene, fluororubber, or the like can be used.

The EC element according to the present embodiment may have a liquid injection port formed of a pair of electrodes and a spacer. After a composition containing the organic compound having an EC property is put in from the liquid injection port and sealed, the injection port is covered with a sealing member and is further hermetically sealed with an adhesive agent or the like, and thereby an element can be obtained. The sealing member has a role of isolating the adhesive agent and the organic compound having the EC property so as to be not in contact with each other.

A method of forming the EC element according to the present embodiment is not particularly limited, and a method for injecting, into a gap provided between a pair of electrode substrates, a liquid including the EC compound prepared in advance by a vacuum injection method, an atmospheric injection method, a meniscus method, or the like may be used.

The EC element 1 according to the present embodiment may have an organic compound according to the present disclosure and the second organic electrochromic compound other than the organic compound. The number of types of the second organic EC compounds may be one or plural, and the second organic compound may be an anodic EC compound colored in an oxidation state, a cathodic EC compound colored in a reduction state, or a compound having both of the above properties. Since the organic compound according to the present disclosure is a compound colored in a reduction state, the second organic EC compound is preferably an anodic electrochromic compound colored in an oxidation state. The anodic EC compound colored in an oxidation state is a compound whose visible light transmittance in an oxidation state is lower than the visible light transmittance in a reduction state. It is only necessary that the transmittance of some visible light region is changed, and it is not necessary that the transmittance of the whole visible light region is changed.

Further, in addition to the second organic EC compound, a third organic EC compound may be further included. By including an organic compound according to the present disclosure or the third organic EC compound exhibiting colored absorption in a wavelength range that is different from that of the second organic EC compound, the light absorption as the EC element can be widely controlled. The third organic EC compound may be an anodic EC compound and may be a cathodic EC compound.

Absorption wavelength regions of the second organic EC compound and the third organic EC compound at decoloring are preferably less than or equal to 400 nm at decoloring. This is because an element having high transparency at decoloring can be provided. On the other hand, an absorption wavelength region at coloring is preferably ranges from 400 nm to 800 nm, and more preferably from 400 nm to 450 nm or from 600 nm to 700 nm.

With the second organic EC compound and the third organic EC compound, the EC element preferably absorbs light in the visible light region at each wavelength uniformly. The second organic EC compound and the third organic EC compound may be the following compound, for example.

The EC compound colored in an oxidation state may be oligothiophenes, a phenazine-based compound such as 5,10-dihydro-5,10-dimethylphenazine or 5,10-dihydro-5,10-di-isopropylphenazine, a metallocene-based compound such as ferrocene, tetra-t-butylferrocene, or titanocene, a phenylenediamine-based compound such as N,N',N,N'-tetramethyl-p-phenylenediamine, a pyrazoline-based compound such as 1-phenyl-2-pyrazolyne, or the like.

The EC compound colored in a reduction state may be a viologen-based compound such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate, or N,N'-diphenyl bipyridinium dihexafluorophosphate, an anthraquinone-based compound such as 2-ethyl anthraquinone, 2-t-butyl anthraquinone, or octamethyl anthraquinone, a ferrocenium salt-based compound such as ferrocenium tetrafluoroborate or ferrocenium hexafluorophosphate, or a styrylated-based compound, or the like.

Among others, a phenazine-based compound and a viologen-based compound are preferable. In the present embodiment, the phenazine-based compound is a compound whose chemical structure includes 5,10-dihydro-phenazine backbone. The phenazine-based compound includes a compound that has a substituent in 5,10-dihydrophenazine. For example, hydrogen atoms at 5 and 10 positions in 5,10-dihydrophenazine may be substituted with an alkyl group such as a methyl group, an ethyl group, or a propyl group, or an aryl group such as a phenyl group, or the like. Further, the phenazine-based compound may be a compound having an alkyl group with 1-20 carbon atoms in 5,10-dihydrophenazine. Further, a compound having an alkoxy group with 1-20 carbon atoms in 5,10-dihydrophenazine may be used. Further, a compound having an aryl group with 4-60 carbon atoms in 5,10-dihydrophenazine may be used. The same applies to other compounds, for example, a viologen-based compound.

It can be confirmed that the compound included in the EC layer 12 in the EC element 1 according to the present embodiment is included in the EC element 1 by being extracted and analyzed using a known method. For example, extraction using chromatography and analysis using NMR may be performed. Further, when the electrochromic layer is a solid, analysis with TOF-SIMS or the like is possible.

The EC element according to the present embodiment has high transparency at decoloring, provides high optical density at coloring, and can reduce the transmittance, and therefore, the EC element can be preferably used in reducing the amount of incident light to an imaging apparatus such as a camera to a large degree.

<<Use of EC Element>>

The EC element 1 according to the present embodiment can be used for an optical filter, a lens unit, an imaging apparatus, a window member, an EC mirror, or the like. In each of the optical filter, the lens unit, the imaging apparatus, the window member, and the EC mirror of the present embodiment, it is possible to provide various absorption colors by using the organic compound expressed by general formula [1] alone or in combination with an EC compound exhibiting a coloring absorption of another wavelength band.

<Optical Filter>

The optical filter according to the present embodiment has the EC element 1 and an active element connected to the EC element 1. The active element is an active element that drives the EC element 1 and adjusts the amount of light passing through the EC element 1. The active element may be, for example, a transistor or a MIM element. The transistor may have semiconductor oxide such as InGaZnO in an active region.

Figure 2:
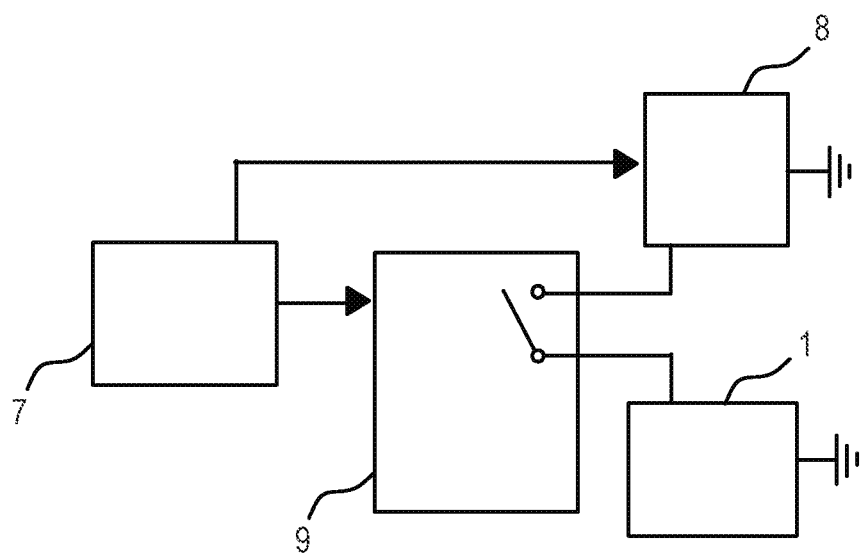
FIG. 2 is a schematic diagram illustrating an example of a drive device connected to the EC element according to the embodiment.

The optical filter may have the EC element 1 according to the present embodiment and a drive device connected to the EC element 1. FIG. 2 is a schematic diagram illustrating an example of the drive device and the EC element 1 driven by the drive device. The drive device of the EC element 1 of the present embodiment has a drive power source 8, a voltage generation unit 9, and a controller 7.

The voltage generation unit 9 may be of a form of generating a square wave voltage by using a comparator or may be of a form of generating a voltage by switching resistors. When resistors are switched to generate a voltage, the voltage generation unit 9 may be referred to as a resistor selector.

Specifically, the voltage generation unit 9 may have a comparator and control the threshold thereof to generate a PWM signal. Further, the voltage generation unit 9 may be configured such that a resistor R1 (not illustrated) and a resistor R2 (not illustrated) having a larger resistance than the resistor R1 are switched so as to be connected in series in the closed circuit including the drive power source 8 and the EC element 1. The resistance of the resistor R1 may preferably be lower than at least the highest impedance in the closed circuit of elements and preferably lower than or equal to 10Ω. The resistance of the resistor R2 may preferably be higher than the highest impedance in the closed circuit of elements and preferably higher than or equal to 1 MΩ. Note that the resistance R2 may be air. In such a case, although the closed circuit appears to be an open circuit in a strict sense, such a circuit can be considered as a closed circuit with the air being regarded as the resistor R2. The controller 7 may transmit a switching signal to the voltage generation unit 9 to control switching between the resistor R1 and the resistor R2.

The drive power source 8 applies, to the EC element 1, a voltage required for the EC material included in the EC layer 12 to generate an electrochemical reaction.

For the method of controlling the transmittance of the EC element 1 performed by the controller 7, a method suitable for an element to be used is employed. Specifically, the method may be a method of inputting a predefined condition to the EC element 1 for a setting value of a desired transmittance or a method of comparing a setting value of transmittance with the transmittance of the EC element 1, selecting a condition so as to be matched to the setting value, and inputting the selected condition. The parameter to be changed may be a voltage, a current, or a duty ratio. The controller 7 increases or decreases the coloring density of a corresponding EC element 1 by increasing or decreasing, for the EC element 1, the voltage if a voltage control scheme is employed, the current if a current control scheme is employed, or the duty ratio if a pulse width modulation scheme is employed. As a result, the incident light can be reduced or increased.

<Lens Unit>

The lens unit according to the present embodiment has an imaging optical system having a plurality of lenses and an optical filter having the EC element 1. The optical filter may be provided either between a plurality of lenses or outside the lens. It is preferable that the optical filter be provided on the optical axis of the lens.

<Imaging Apparatus>

The imaging apparatus of the present embodiment has an optical filter and a light receiving element that receives light that has passed through the optical filter. Specifically, the imaging apparatus may be a camera, a video camera, a mobile phone with a camera, or the like. The imaging apparatus may be formed such that an imaging unit having the light receiving element and a lens unit having one or more lenses can be separated from each other. Herein, when the imaging apparatus is configured such that the imaging unit and the lens unit can be separated from each other, the present disclosure also includes a form in which an optical filter that is a separate member from the imaging unit is used at image capturing. Note that, in such a case, a position where the optical filter is arranged may be outside the lens unit, between the lens unit and the light receiving element, between a plurality of lenses (if the lens unit has a plurality of lenses), or the like.

Figure 3A:
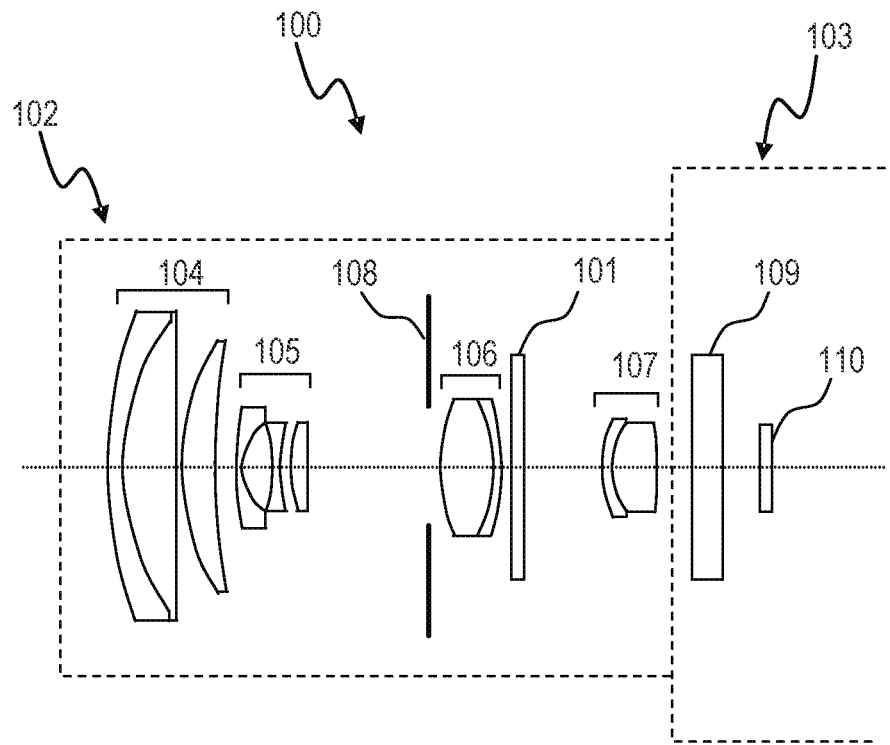
FIG. 3A and FIG. 3B are schematic diagrams each illustrating an example of an imaging apparatus according to the embodiment.
Figure 3B:
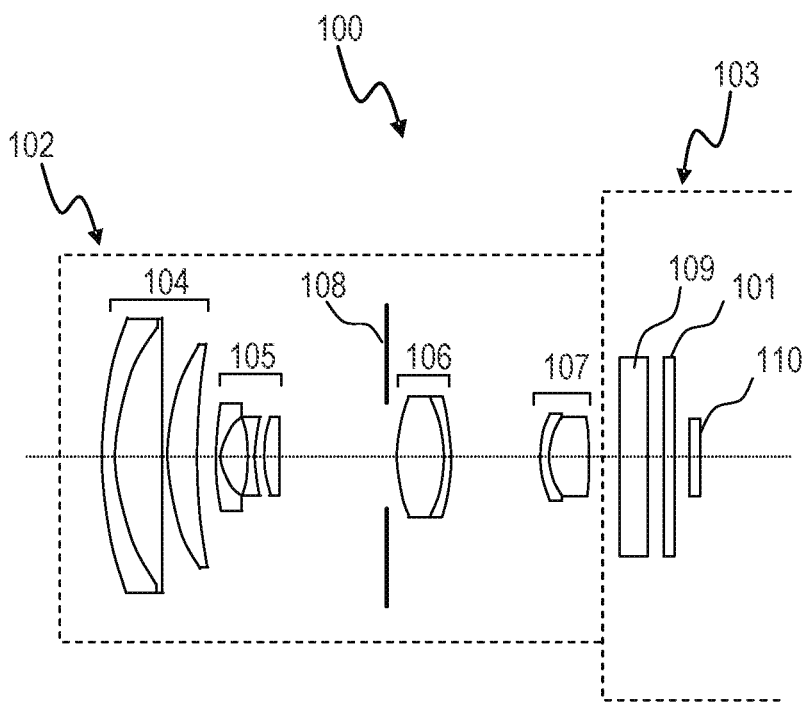

FIG. 3A and FIG. 3B are schematic diagrams each illustrating an example of the configuration of an imaging apparatus 100 using the optical filter of the present embodiment. Each imaging apparatus 100 of FIG. 3A and FIG. 3B is an imaging apparatus having a lens unit 102 and an imaging unit 103. In FIG. 3A, the optical filter 101 is arranged in the lens unit 102, and in FIG. 3B, the optical filter 101 is arranged in the imaging unit 103.

First, the imaging apparatus 100 of FIG. 3A will be described. The lens unit 102 has the optical filter 101 and an imaging optical system having a plurality of lenses or a lens group. The optical filter 101 is the optical filter of the present embodiment described above. The lens unit 102 is connected to the imaging unit 103 in a detachable manner via a mount member (not illustrated).

The lens unit 102 is a zoom lens of a rear focus scheme to perform focusing in the rear of an aperture. The lens unit 102 has four lens groups of a first lens group 104 having a positive refractive force, a second lens group 105 having a negative refractive force, a third lens group 106 having a positive refractive force, and a fourth lens group 107 having a negative refractive force in this order from an object side. The gap between the second lens group 105 and the third lens group 106 is changed to perform magnification, and a group of lenses of the fourth lens group 107 is moved to perform focusing. The lens unit 102 has an aperture 108 between the second lens group 105 and the third lens group 106 and has the optical filter 101 between the third lens group 106 and the fourth lens group 107, for example. The lens unit 102 is configured such that the light that has passed through the lens unit 102 passes through respective lens groups 104 to 107, the aperture 108, and the optical filter 101, and adjustment of the light amount using the aperture 108 and the optical filter 101 can be performed.

Note that, although the optical filter 101 is arranged between the third lens group 106 and the fourth lens group 107 inside the lens unit 102 in FIG. 3A, the configuration is not limited thereto. For example, the optical filter 101 may be either in front of the aperture 108 (on the object side) or in rear thereof (on the imaging unit 103 side) or may be either in front or rear of any one of the first to fourth lens groups 104 to 107 or between the lens groups. Note that, with the optical filter 101 being arranged at a position where light is converged, there is an advantage such as a smaller area of the optical filter 101.

Further, the configuration of the lens unit 102 is not limited to the configuration described above and may be selected as appropriate. For example, a rear focus scheme as well as an inner focus scheme to perform focusing in front of the aperture may be employed, or another scheme may be employed. Further, a special lens other than a zoom lens, such as a fisheye lens, a macro lens, or the like may be selected as appropriate.

The imaging unit 103 has a glass block 109 and a light receiving element 110. The glass block 109 is a glass block such as a low-pass filter, a phase plate, a color filter, or the like. Further, the light receiving element 110 is a sensor unit that receives light that has passed through the lens unit, and an image pickup device such as a CCD or a CMOS can be used. Further, an optical sensor such as a photodiode may be used, and an element or a device that acquires and outputs information on the intensity or the wavelength of light may be utilized as appropriate.

As illustrated in FIG. 3A, when the optical filter 101 is embedded in the lens unit 102, the drive device may be arranged inside the lens unit 102 or may be arranged outside the lens unit 102. When the drive device is arranged outside the lens unit 102, the EC element 1 inside the lens unit 102 is connected to the drive device via a wiring and driven and controlled.

Further, in the configuration of the imaging apparatus 100 of FIG. 3A, the optical filter 101 is arranged inside the lens unit 102. However, the present disclosure is not limited to such a form, and any form may be employed as long as the optical filter 101 is arranged in a suitable part inside the imaging apparatus 100 and the light receiving element 110 is arranged so as to receive light that has passed through the optical filter 101.

In FIG. 3B, the imaging unit 103 has the optical filter 101. FIG. 3B is the same as FIG. 3A except that the position of the optical filter 101 is different. In FIG. 3B, the optical filter 101 is arranged immediately in front of the light receiving element 110. When the optical filter 101 is built in the imaging unit 103, since the lens unit 102 to be connected is not required to have the optical filter 101, a dimmable imaging apparatus using the existing lens unit 102 can be formed.

The imaging apparatus 100 of the present embodiment is applicable to a product having a combination of an optical filter and a light receiving element. For example, the imaging apparatus 100 can be used for a camera, a digital camera, a video camera, or a digital video camera and can be applied to a product having a built-in imaging apparatus, such as a mobile phone or a smartphone, a PC, a tablet, or the like. Further, according to the imaging apparatus 100 of the present embodiment, by using the optical filter 101 as a dimming member, it is possible to suitably change the dimming amount by using a single filter, and there is an advantage of reduction in the number of components or space saving.

<Window Member>

Further, the EC element 1 according to the present embodiment can also be used for a window member. The window member according to the present embodiment has the EC element 1 and an active element connected to the EC element 1. The active element is an active element that drives the EC element 1 and adjusts the light amount of light passing through the EC element 1. The active element may be, for example, a transistor or a MIM element. The transistor may have semiconductor oxide such as InGaZnO in the active region.

Figure 4A:
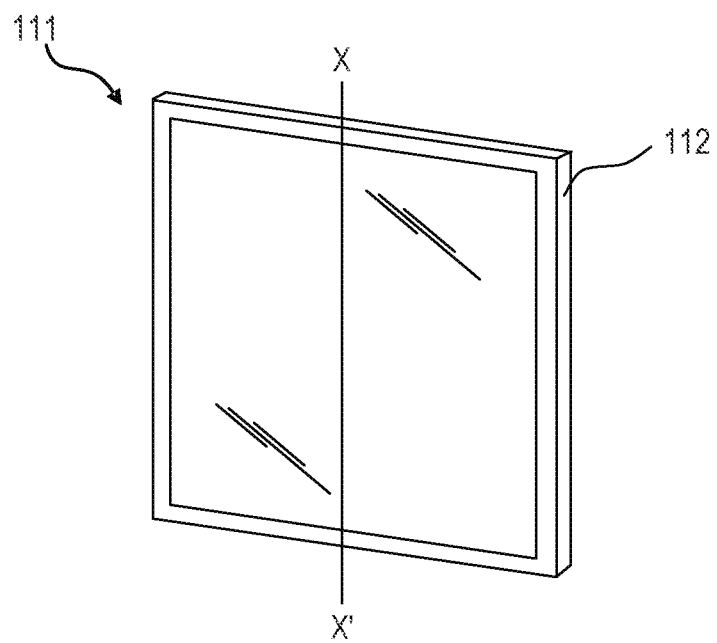
FIG. 4A and FIG. 4B are schematic diagrams illustrating an example of a window member according to the embodiment.
Figure 4B:
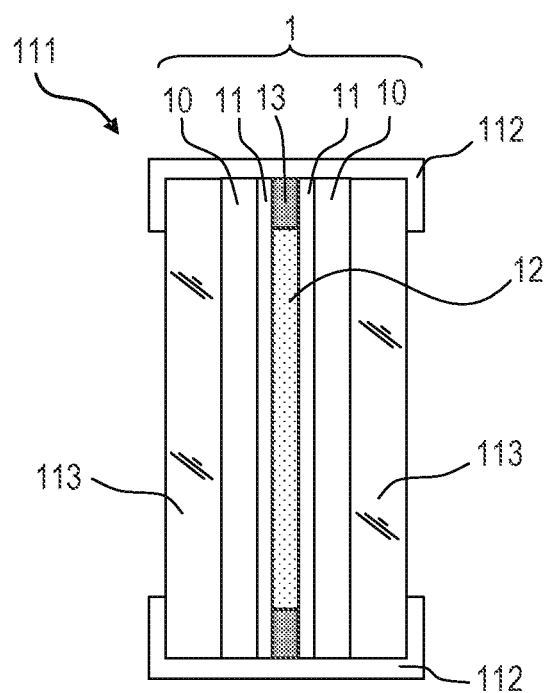

FIG. 4A is a perspective view illustrating a window member using the EC element 1 according to the present embodiment, and FIG. 4B is a schematic diagram illustrating a sectional view taken along a line X-X' of FIG. 4A.

A dimming window 111 of the present embodiment is formed of the EC element 1 (optical filter), a transparent plate 113 interposing and holding the EC element 1, and a frame 112 surrounding the whole structure to be integrated. The EC element 1 has a drive device (not illustrated), and the drive device may be integrated inside the frame 112 or may be arranged outside the frame 112 and connected to the EC element 1 via a wiring.

The frame 112 may be a general frame having a form that covers and is integrated with at least a part of the EC element 1. The material of the frame 112 may be any material, and a resin of polycarbonate, acrylonitrile butadiene styrene, polyalkylene furan dicarboxylate, polylactic acid, polybutadiene terephthalate, or the like or a mixture thereof may be used.

The transparent plate 113 is not particularly limited as along as the material thereof has high light transmittance and is preferably a glass material when taking a use as a window into consideration. Although the EC element 1 is a component member separate from the transparent plate 113 in FIG. 4A and FIG. 4B, the transparent substrate 10 of the EC element 1 may be regarded as the transparent plate 113, for example.

Such a dimming window can be applied to a use for adjusting the incidence amount of the sunlight in daytime into a room, for example. Such a dimming window can also be applied to adjustment of the heat amount of the sun as well as the light amount thereof and thus can be used for control of the brightness or the temperature inside a room. Further, such a dimming window is applicable to a use as a shutter for blocking a view from the outside of a room to the inside of the room. Such a dimming window is applicable not only to a glass window for a building but also to a window of a vehicle such as an automobile, a train, an airplane, a ship, or the like.

<EC Mirror>

When the EC element according to the present embodiment and a light reflection member are provided and the EC element is arranged on a light reflection surface of the light reflection member, an electrochromic mirror can be provided. The light reflection member may serve as an electrode or a substrate of the EC element.

EXAMPLES

While the present disclosure will be more specifically described below with reference to examples, the present disclosure is not limited thereto.

Example 1

Synthesis of Exemplary Compound B-4

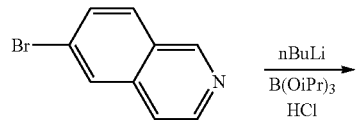

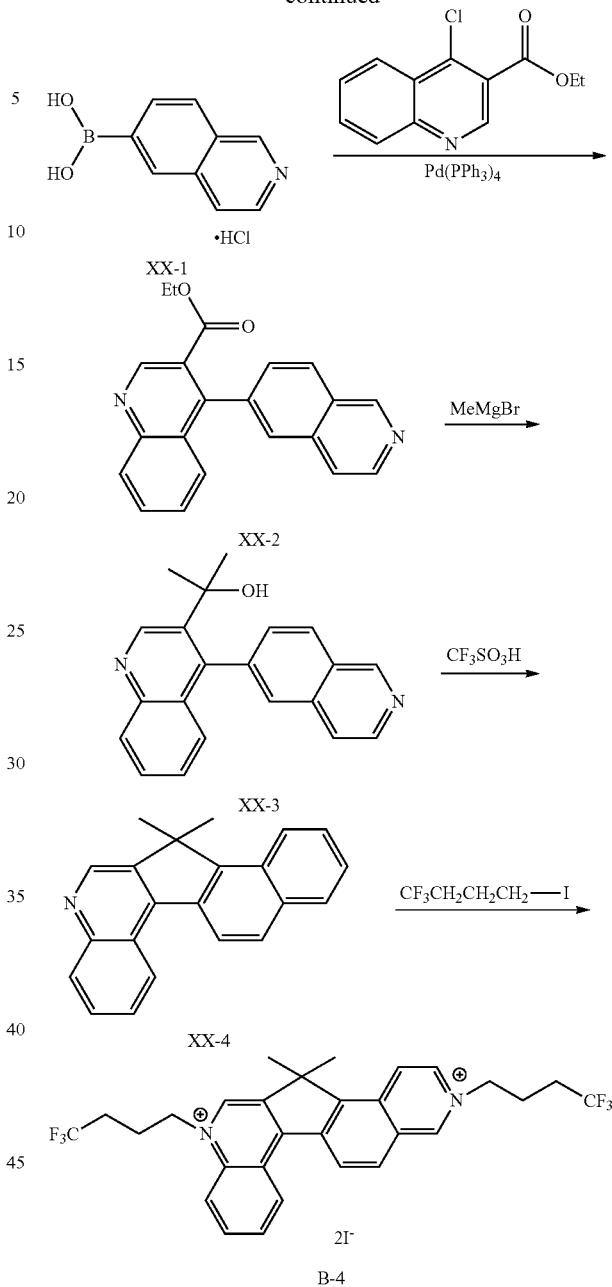

(1) Synthesis of XX-1

In a 100 mL reaction container, 6-bromo-isoquinoline: 3.75 g (18.0 mmol) and triisopropyl borate: 4.06 g (21.6 mmol) were mixed in anhydrous tetrahydrofuran (50 ml), and the mixture was cooled to −70 degrees Celsius. Next, an n-butyllithium solution: 12.4 ml (approximately 1.6 M of hexane solution, 19.8 mmol) was put in the reaction container in drops, and the mixture was stirred for 1 hour and then elevated to room temperature. Furthermore, after 15 ml of 5N of hydrochloric acid was added and the mixture was reacted at room temperature for 1 hour, the precipitated solid was filtered to obtain an XX-1 (1.86 g, yield 49%).

(2) Synthesis of XX-2

In a 200 ml reactor, the XX-1: 1.47 g (7.0 mmol) and ethyl 4-chloroquinoline-3-carboxylate: 1.51 g (6.4 mmol) were mixed in 1,4-dioxane (75 ml), and dissolved oxygen was removed with nitrogen. Next, an aqueous solution (25 ml) of Pd (PPh3)4: 370 mg (0.32 mmol) and potassium carbonate: 2.65 g (19.2 mmol) was added under a nitrogen atmosphere, and the mixture was reacted at 90 degrees Celsius for 5 hours. After water was added to the reaction solution to stop the reaction, the aqueous layer was extracted with ethyl acetate and separated and purified by silica gel chromatography (mobile phase: hexane/ethyl acetate) to obtain a solid XX-2 (1.49 g, yield 71%).

(3) Synthesis of XX-3

In a 200 ml reactor, the XX-2: 1.49 g (4.5 mmol) was mixed in anhydrous tetrahydrofuran (50 ml), and the mixture was cooled to −5 degrees Celsius. Next, methylmagnesium bromide solution: 36 ml (approximately 1.0 M of tetrahydrofuran solution, 36 mmol) was slowly put in the reactor in drops, and the mixture was stirred for 2 hours and then elevated to room temperature. After water was added to this solution to stop the reaction, the aqueous layer was extracted with ethyl acetate and separated and purified by silica gel chromatography (mobile phase: chloroform/methanol) to obtain a solid XX-3 (1.31 g, yield 92%).

(4) Synthesis of XX-4

In a 50 ml reaction container, the XX-3 (1.2 g, 3.8 mmol) and trifluoromethanesulfonic acid (12 mL) were mixed, and the mixture was stirred at room temperature for 4 hours. After this solution was neutralized with a sodium hydroxide aqueous solution, the aqueous layer was extracted with ethyl acetate and separated and purified by silica gel chromatography (mobile phase: chloroform/methanol) to obtain a solid XX-4 (0.88 g, yield 78%).

(5) Synthesis of B-4

To a reaction container, the XX-4 (200 mg, 0.67 mmol), 1,1,1-trifluoro-4-iodobutane: 1.61 g (6.7 mmol), and 4 ml of 2-methoxyethanol were added, and the mixture was heated and refluxed at 110 degrees Celsius and reacted for 20 hours. After the reaction was completed, ethyl acetate was added, and the precipitated crystals were filtered to obtain an exemplary compound B-4 (355 mg, yield 68%).

The structure of the obtained compound was confirmed by the measurement of nuclear magnetic resonance spectrum (NMR) measurement. As a result, since the ratio of peak integration values sufficiently matched the structure of B-4, it was confirmed that the obtained compound was the exemplary compound B-4. The measurement results of the NMR spectrum are indicated below.

$^1$H-NMR (MeOD) δ (ppm): 10.25 (s, 1H), 10.10 (s, 1H), 9.47 (d, 2H), 9.11 (d, 1H), 8.95 (d, 1H), 8.83 (d, 1H), 8.74 (d, 1H), 8.40 (t, 1H), 8.28 (t, 1H), 5.30 (t, 2H), 4.96 (t, 2H), 2.63-2.42 (m, 8H), 2.07 (s, 6H).

Example 2

Synthesis of Exemplary Compound B-5

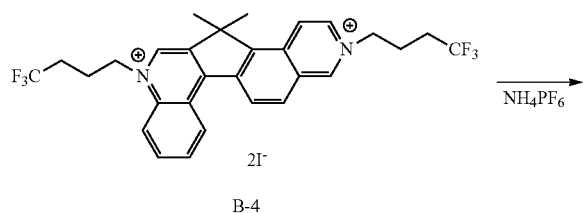

B-4

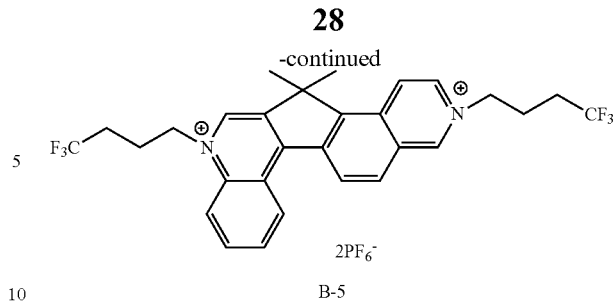

B-5

The exemplary compound B-4 (200 mg, 0.26 mmol) synthesized in Example 1 was dissolved in water. An aqueous solution in which 320 mg of ammonium hexafluorophosphate was dissolved was put in drops, and the mixture was stirred at room temperature for 3 hours. The precipitated crystals were filtered and washed with water, isopropyl alcohol, and diethyl ether sequentially to obtain an exemplary compound B-5 (195 mg, yield: 93%). The structure of this compound was confirmed by NMR measurement.

$^1$H-NMR (DMSO-d$_6$) δ (ppm): 10.31 (s, 1H), 10.18 (s, 1H), 9.48 (d, 2H), 9.15 (d, 1H), 8.99 (d, 1H), 8.83 (d, 1H), 8.79 (d, 1H), 8.39 (t, 1H), 8.24 (t, 1H), 5.22 (t, 2H), 4.87 (t, 2H), 2.66-2.25 (m, 8H), 1.93 (s, 6H).

Example 3

Synthesis of Exemplary Compound B-8

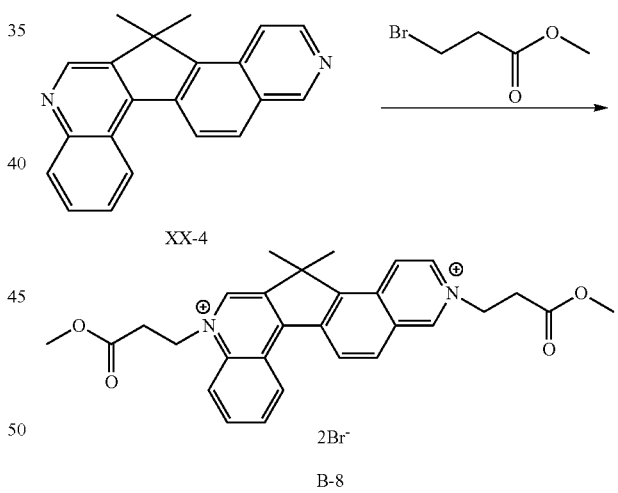

B-8

In a reaction container, the XX-4 (116 mg, 0.39 mmol) synthesized in Example 1, methyl 3-bromopropionate (784 mg, 4.70 mmol), and 2 ml of 2-methoxyethanol were added, and the mixture was heated and refluxed at 110 degrees Celsius and reacted for 40 hours. After the reaction was completed, ethyl acetate was added, and the precipitated crystals were filtered to obtain an exemplary compound B-8 (170 mg, yield 69%). The structure of this compound was confirmed by NMR measurement.

$^1$H-NMR (DMSO-d$_6$) δ (ppm): 10.38 (s, 1H), 10.27 (s, 1H), 9.48 (d, 2H), 9.15 (d, 1H), 9.02 (d, 1H), 8.84 (d, 1H), 8.80 (d, 1H), 8.38 (t, 1H), 8.26 (t, 1H), 5.43 (t, 2H), 5.07 (t, 2H), 3.64 (s, 6H), 3.39-3.30 (m, 4H), 1.97 (s, 6H).

Example 4

Synthesis of Exemplary Compound B-9

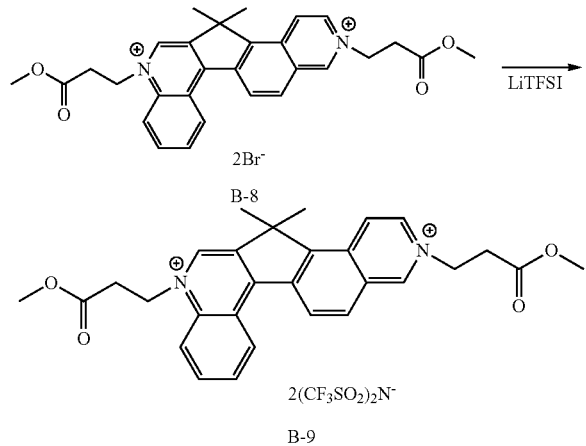

The exemplary compound B-8 (160 mg, 0.25 mmol) synthesized in Example 3 was dissolved in water. An aqueous solution in which 560 mg of bis (trifluoromethanesulfonyl) imide lithium was dissolved was put in drops, and the mixture was stirred at room temperature for 3 hours. The precipitated crystals were filtered and washed with water, isopropyl alcohol, and diethyl ether sequentially to obtain an exemplary compound B-9 (220 mg, yield: 84%). The structure of this compound was confirmed by NMR measurement.

$^1$H-NMR (CD$_3$CN) δ (ppm): 9.85 (s, 1H), 9.63 (s, 1H), 9.29 (d, 1H), 9.23 (d, 1H), 8.85 (d, 1H), 8.71 (d, 2H), 8.51 (d, 1H), 8.33 (t, 1H), 8.22 (t, 1H), 5.33 (t, 2H), 5.00 (t, 2H), 3.63 (s, 6H), 3.27-3.18 (m, 4H), 1.94 (s, 6H).

Example 5

Synthesis of Exemplary Compound B-17

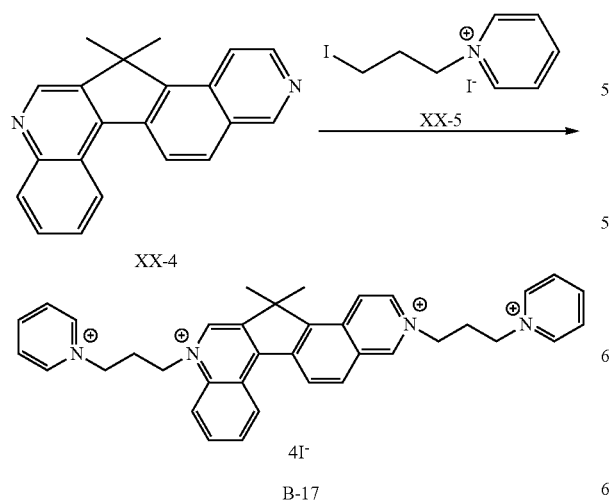

In a reaction container, the XX-4 (293 mg, 0.99 mmol) and the XX-5 (2.97 g, 7.91 mmol) synthesized in Example 1 and 6 ml of N,N-dimethylformamide were added, and the mixture was heated and refluxed at 100 degrees Celsius and reacted for 24 hours. After the reaction was completed, ethyl acetate was added, and the precipitated crystals were filtered to obtain an exemplary compound B-17 (950 mg, yield 92%). The structure of this compound was confirmed by NMR measurement.

$^1$H-NMR (DMSO-d$_6$) δ (ppm): 10.38 (s, 1H), 10.31 (s, 1H), 9.54 (d, 1H), 9.51 (d, 1H), 9.20 (d, 1H), 9.15 (d, 4H), 9.00 (d, 1H), 8.84 (dd, 2H), 8.68 (t, 2H), 8.42 (t, 1H), 8.28 (t, 1H), 8.24 (q, 4H), 5.34 (t, 2H), 5.00-4.89 (m, 4H), 4.84 (t, 2H), 2.88-2.75 (m, 4H), 1.99 (s, 6H).

Example 6

Synthesis of Exemplary Compound B-18

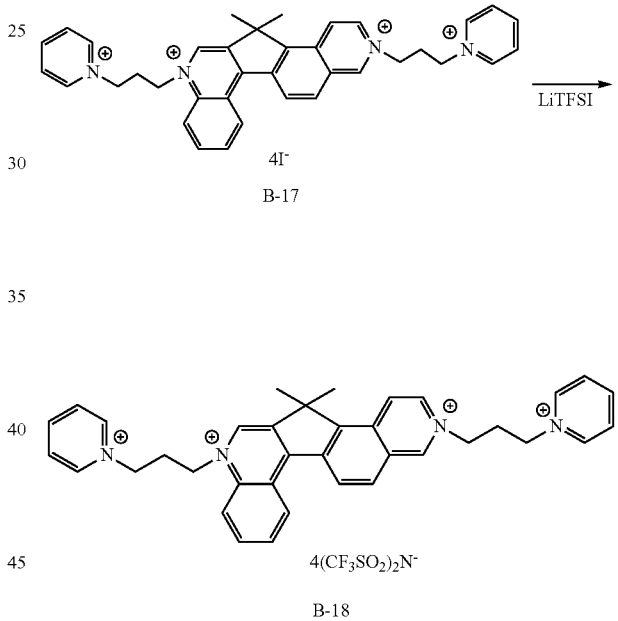

The exemplary compound B-17 (350 mg, 0.33 mmol) synthesized in Example 5 was dissolved in water. An aqueous solution in which 900 mg of bis (trifluoromethanesulfonyl) imide lithium was dissolved was put in drops, and the mixture was stirred at room temperature for 3 hours. The precipitated crystals were filtered and washed with water, isopropyl alcohol, and diethyl ether sequentially to obtain the exemplary compound B-18 (417 mg, yield: 80%). The structure of this compound was confirmed by NMR measurement.

$^1$H-NMR (DMSO-d$_6$) δ (ppm): 10.31 (s, 1H), 10.14 (s, 1H), 9.52 (d, 1H), 9.49 (d, 1H), 9.17 (d, 1H), 9.11 (d, 2H), 9.09 (d, 2H), 8.98 (d, 1H), 8.82 (d, 2H), 8.68 (t, 2H), 8.42 (t, 1H), 8.28 (t, 1H), 8.24 (q, 4H), 5.29 (t, 2H), 4.92 (t, 2H), 4.87 (t, 2H), 4.82 (t, 2H), 2.86-2.72 (m, 4H), 1.96 (s, 6H).

Example 7

Synthesis of Exemplary Compound A-6

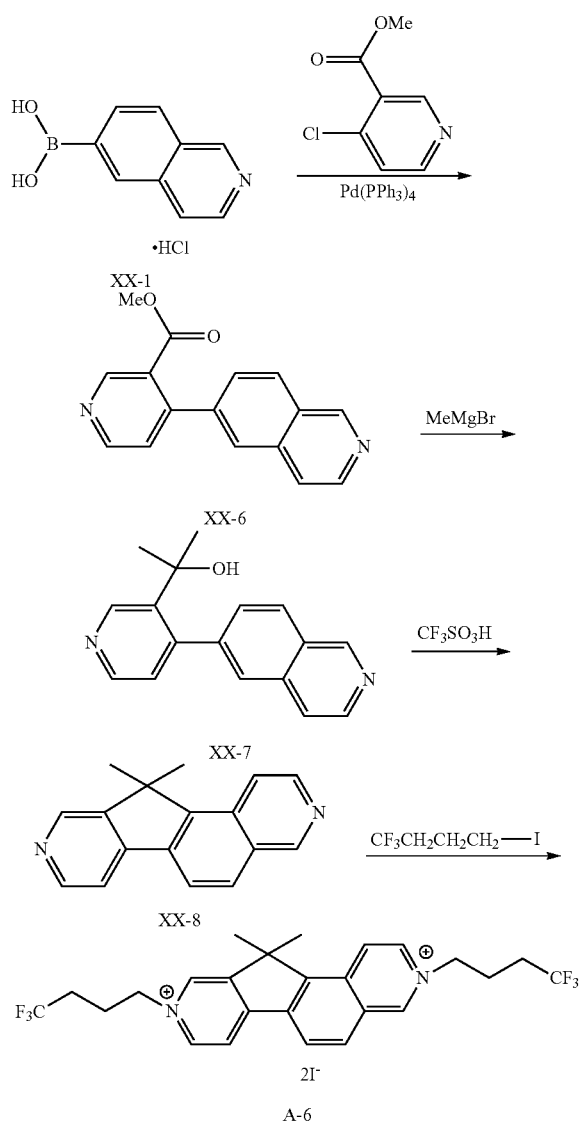

(1) Synthesis of XX-6

In a 100 ml reactor, the XX-1: 250 mg (1.19 mmol) synthesized in Example 1 and methyl 4-chloropyridine-3-carboxylate: 186 mg (1.09 mmol) were mixed in 1,4-dioxane (12 ml), and dissolved oxygen was removed with nitrogen. Next, an aqueous solution (4 ml) of Pd (PPh$_3$)4: 63 mg (0.054 mmol) and potassium carbonate: 450 mg (3.26 mmol) was added under a nitrogen atmosphere, and the mixture was reacted at 90 degrees Celsius for 5 hours. After water was added to the reaction solution to stop the reaction, the aqueous layer was extracted with ethyl acetate and separated and purified by silica gel chromatography (mobile phase: hexane/ethyl acetate) to obtain a solid XX-6 (170 mg, yield 59%).

(2) Synthesis of XX-7

In a 100 ml reactor, the XX-6: 170 mg (0.64 mmol) was mixed in anhydrous tetrahydrofuran (8 ml), and the mixture was cooled to −5 degrees Celsius. Next, methylmagnesium bromide solution: 1.7 ml (approximately 3.0 M of tetrahydrofuran solution, 5 mmol) was slowly put in the reactor in drops, and the mixture was stirred for 2 hours and then elevated to room temperature. After water was added to this solution to stop the reaction, the aqueous layer was extracted with ethyl acetate and separated and purified by silica gel chromatography (mobile phase: chloroform/methanol) to obtain a solid XX-7 (115 mg, yield 68%).

(3) Synthesis of XX-8

In a 50 ml reaction container, the XX-7 (115 mg, 0.44 mmol) and trifluoromethanesulfonic acid (1.2 mL) were mixed, and the mixture was stirred at room temperature for 20 hours. After this solution was neutralized with a sodium hydroxide aqueous solution, the aqueous layer was extracted with ethyl acetate and separated and purified by silica gel chromatography (mobile phase: chloroform/methanol) to obtain a solid XX-8 (70 mg, yield 65%).

(4) Synthesis of A-6

To a reaction container, the XX-8 (32 mg, 0.13 mmol), 1,1,1-trifluoro-4-iodobutane: 185 mg (0.78 mmol), and 2 ml of acetonitrile were added, and the mixture was heated and refluxed at 80 degrees Celsius and reacted for 24 hours. After the reaction was completed, ethyl acetate was added, and the precipitated crystals were filtered to obtain an exemplary compound A-6 (80 mg, yield 85%). The structure of this compound was confirmed by NMR measurement.

$^1$H-NMR (DMSO-d$_6$) δ (ppm): 10.26 (s, 1H), 9.70 (s, 1H), 9.26 (d, 1H), 9.07 (d, 1H), 8.98 (d, 2H), 8.90 (d, 1H), 8.72 (d, 1H), 4.87 (t, 2H), 4.75 (t, 2H), 2.48-2.27 (m, 8H), 1.89 (s, 6H).

Example 8

Synthesis of Exemplary Compound A-7

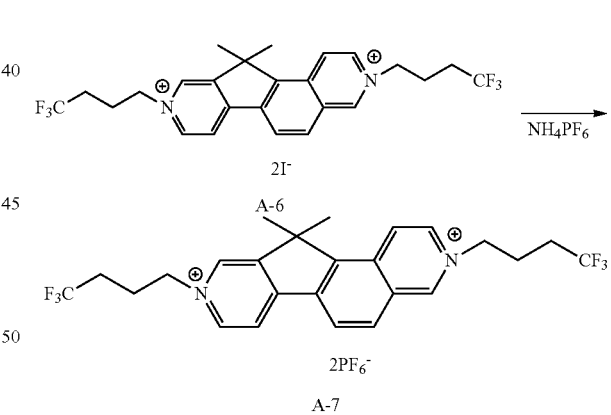

The exemplary compound A-6 (80 mg, 0.11 mmol) synthesized in Example 6 was dissolved in water. An aqueous solution in which 160 mg of ammonium hexafluorophosphate was dissolved was put in drops, and the mixture was stirred at room temperature for 3 hours. The precipitated crystals were filtered and washed with water, isopropyl alcohol, and diethyl ether sequentially to obtain an exemplary compound A-7 (78 mg, yield: 93%). The structure of this compound was confirmed by NMR measurement.

$^1$H-NMR (DMSO-d$_6$) δ (ppm): 10.24 (s, 1H), 9.67 (s, 1H), 9.24 (d, 1H), 9.06 (d, 1H), 8.97 (d, 1H), 8.96 (d, 1H), 8.89 (d, 1H), 8.72 (d, 1H), 4.86 (t, 2H), 4.74 (t, 2H), 2.48-2.26 (m, 8H), 1.89 (s, 6H).

Example 9

Evaluation of EC Characteristics

With respect to the exemplary compound B-18 of Example 6, change in the optical spectrum due to application of a voltage was measured.

The measurement was performed by using a solution in which the exemplary compound B-18 was dissolved ($2.0 \times 10^{-3}$ mol/L) in a propylene carbonate solution (0.1 mol/L) of tetrabutylammonium hexafluorophosphate as a supporting electrolyte. The measurement was performed by putting this solution in a glass cell having an optical path length of 1 mm, aligning a mesh-shaped platinum electrode (working electrode) and a wire-shaped platinum electrode (counter electrode), and arranging a reference electrode RE (Ag/Ag$^+$).

The optical spectrum measurement was performed by using a transmitted light passing through the mesh electrode by performing constant potential reduction on the solution at a potential that is higher than or equal to the reduction potential of the compound. A potentiostat (CellTest 1470E) manufactured by Solartron Analytical was used for application of the voltage, and a spectroscope (USB2000-UV-VIS) manufactured by Ocean Optics was used for the spectrometry.

In a decolored state, the exemplary compound B-18 exhibited no absorption in the whole visible light region and was a highly transparent material. On the other hand, at reduction coloring in response to the application of a voltage, the transmittance changed within the visible range, and the wavelength λmax of the absorption peak thereof was 544 nm. This reduction colored state returned to be colorless and transparent due to oxidation, and reversible EC characteristics due to oxidation-reduction were confirmed.

Example 10

Evaluation of EC Characteristics

The measurement was performed in the same method as in Example 9 except that the exemplary compound A-7 of Example 8 was used instead of the exemplary compound B-18. Also in the exemplary compound A-7, the transmittance changed within the visible range at reduction coloring in response to the application of a voltage, and the wavelength λmax of the absorption peak thereof was 498 nm. This reduction colored state returned to be colorless and transparent due to oxidation, and reversible EC characteristics due to oxidation-reduction were confirmed.

Example 11

<Manufacturing of EC Element>

The exemplary compound B-5 as a cathodic EC material and W-1 (5,10-diisopropyl-5,10-dihydrophenazine) having the structure below as an anodic EC material were dissolved in propylene carbonate at a concentration of 100 mM, respectively. Furthermore, 5 wt % of polymethylmethacrylate (PMMA) was added as a thickener, and an EC solution was prepared.

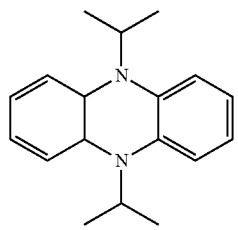

W-1

Next, two sheets of transparent conductive glasses on which an indium-doped tin oxide (ITO) film was formed were prepared and arranged such that the ITO films face each other. Then, the outer circumferences of the two sheets of transparent conductive glasses were adhered to each other using an epoxy-based seal material mixed with spacer beads having a particle diameter of 50 μm. By injecting a solution in which an anodic EC compound and a cathodic EC compound were dissolved from an injection port formed in advance on the transparent conductive glasses, the space formed by the two sheets of transparent conductive glasses and the seal material was filled with the solution. Then, the injection port was sealed with a UV curable type seal material to obtain an EC element.

<Evaluation of Element Characteristics>

Figure 5:
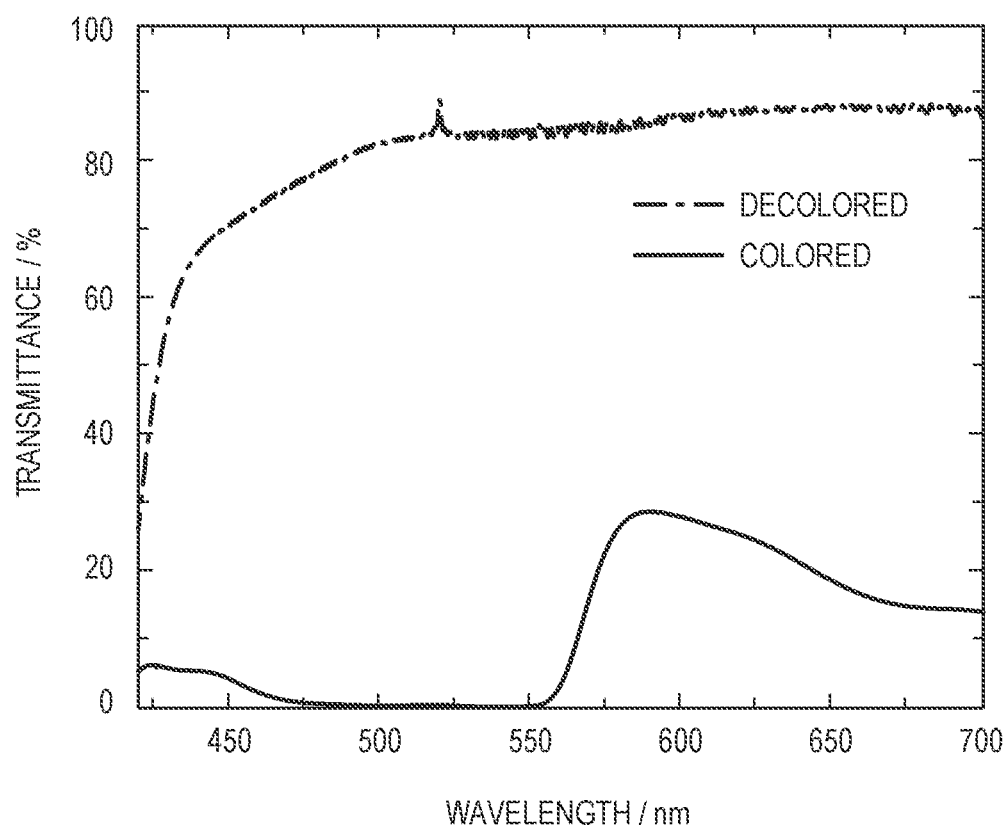
FIG. 5 is a diagram illustrating transmittance spectra in a decolored state and a colored state of an EC element of Example 11.

When a drive voltage of 0.9 V was applied to the above EC element, absorption due to the reduced species of the exemplary compound B-5 (λ=544 nm) and absorption due to the oxidized species of the anodic EC compound W-1 (λ=480 nm) were exhibited, and the EC element was colored. The EC element was decolored when 0 V was applied, and reversible coloring/decoloring was exhibited. FIG. 5 illustrates the change in the transmittance spectrum of the EC element of the present example in response to the application of the voltage.

<High-Temperature Durability Test>

In a test, a coloring/decoloring cycle test of the EC element was performed in a thermostatic oven at 80 degrees Celsius. Specifically, a test to repeat coloring/decoloring for 20 cycles at a constant temperature of 80 degrees Celsius with the on/off time periods of the voltage in one cycle being 10,000 seconds/1,000 seconds was performed.

Figure 6:
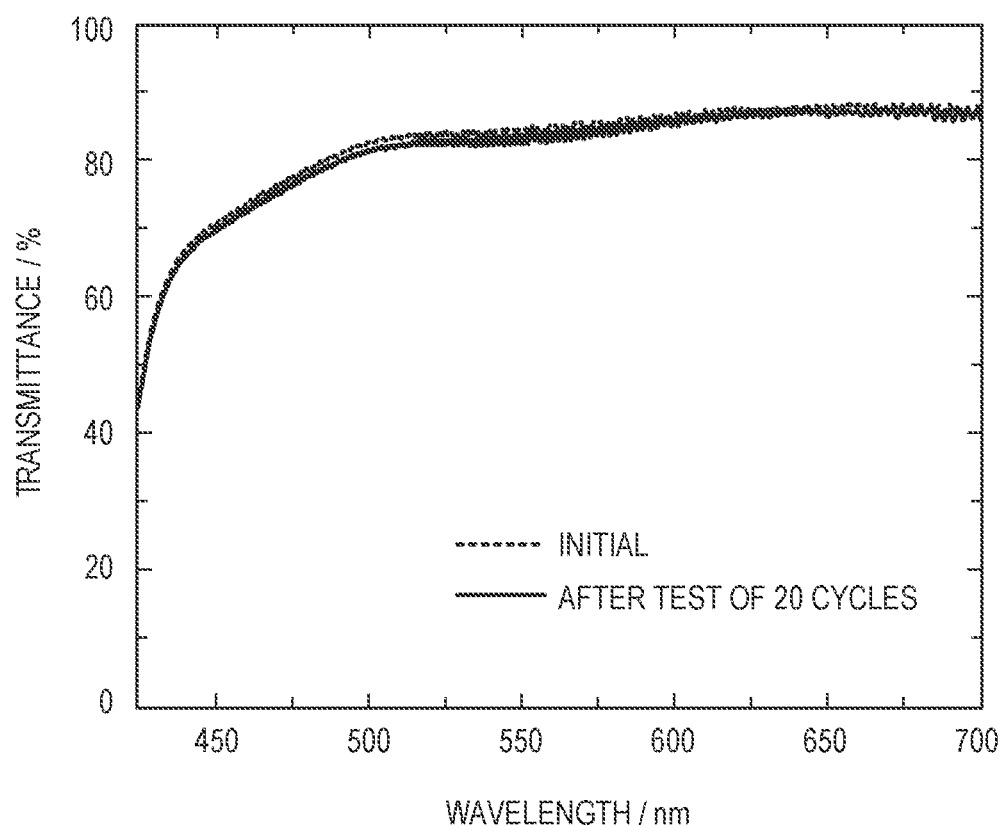
FIG. 6 is a diagram illustrating transmittance spectra in a decolored state of an EC element before and after a high-temperature drive durability test of Example 11.
Figure 7:
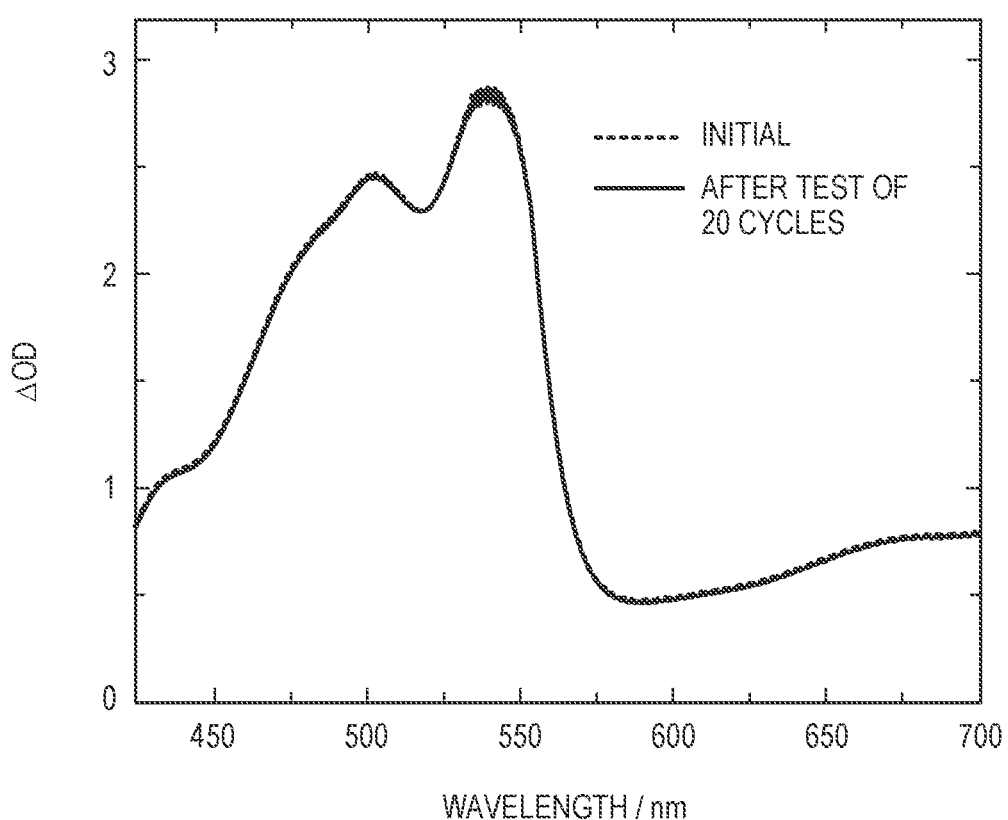
FIG. 7 is a diagram illustrating absorption spectra in a colored state of an EC element before and after a high-temperature drive durability test of Example 11.

FIG. 6 illustrates the transmittance spectrum at decoloring in the initial state and after 20 cycles, and FIG. 7 illustrates the absorption spectrum at coloring in the initial state and after 20 cycles. As illustrated in FIG. 6, the transmittance spectrum at decoloring did not substantially change before and after the durability test, and the change in the average transmittance in the wavelength range from 450 nm to 700 nm was −0.6%. Further, as illustrated in FIG. 7, the absorption spectrum at coloring did not substantially change before and after the durability test, and the maximum value of AOD change was −1.2%, and substantially no deterioration was found. The result is indicated in Table 1.

Examples 12 to 14, Comparative Example 1

An EC element using a compound indicated in Table 1 instead of the exemplary compound B-5 as a cathodic EC compound was manufactured in the same manner as in Example 11, and a high-temperature drive durability test was performed in the same manner as in Example 11. The structure of a compound Ref-1 is illustrated below.

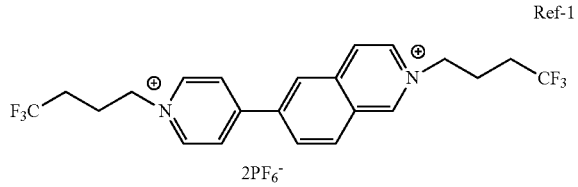 [SMILES: FC(F)(F)CCC[n+]1ccc(-c2ccc3c[n+](CCCC(F)(F)F)ccc3c2)cc1]

Ref-1

Table 1 illustrates the results of the spectrum change before and after the test. As indicated in Table 1, in the EC element of the comparative example 1, a significant degradation tendency was confirmed, specifically, the change in transmittance at decoloring after the high-temperature durability test was −38.5%, and the AOD change at coloring after the high-temperature durability test was −66.3%. It is considered that, since the compound Ref-1 has no crosslinked structure at the EC site in which a pyridine ring and an isoquinoline ring are coupled to each other and the flatness is low, the stability as a molecule is low, and the drive durability at a high temperature is low.

TABLE 1

| Compound | | Average transmittance change at decoloring | Maximum value of ΔOD change at coloring |
| --- | --- | --- | --- |
| Example 11 | Exemplary compound B-5 | −0.6% | −1.2% |
| Example 12 | Exemplary compound B-18 | −0.5% | −1.1% |

TABLE 1-continued

| Compound | | Average transmittance change at decoloring | Maximum value of ΔOD change at coloring |
| --- | --- | --- | --- |
| Example 13 | Exemplary compound B-9 | −1.2% | −2.0% |
| Example 14 | Exemplary compound A-7 | −0.7% | −1.9% |
| Comparative example 1 | Compound Ref-1 | −38.5% | −66.3% |

Example 15

Synthesis of Exemplary Compound A-18

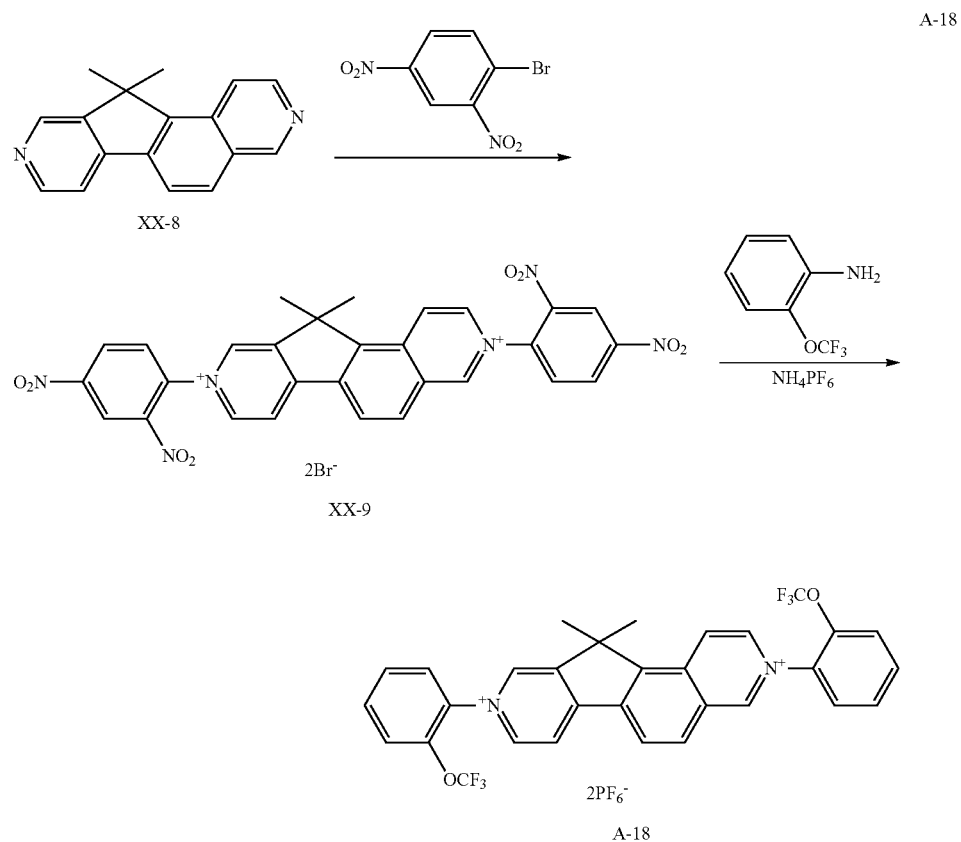

A-18

(1) Synthesis of XX-9

In a reaction container, the XX-8 (38 mg, 0.15 mmol) synthesized in Example 7, 2,4-dinitrobromobenzene: 191 mg (0.77 mmol), and 2 ml of isopropyl alcohol were added, and the mixture was heated and refluxed at 80 degrees Celsius and reacted for 24 hours. After the reaction was completed, ethyl acetate was added and the precipitated crystals were filtered to obtain an intermediate XX-9 (105 mg, yield 92%).

(2) Synthesis of A-18

In a reaction container, the XX-9 (100 mg, 0.135 mmol), 2-trifluoromethoxyaniline: 202 mg (1.14 mmol), and 1.5 ml of methoxyethanol were added, and the mixture was heated under refluxed at 100 degrees Celsius and reacted for 24 hours. After the reaction was completed, ethyl acetate was added to precipitate deposits, and the precipitate was washed with acetonitrile. The powder thereof was dissolved in water, an aqueous solution in which 120 mg of ammonium hexafluorophosphate was dissolved was put in the reaction container in drops, and the mixture was stirred at room temperature for 3 hours. The precipitated crystals were filtered and washed with water, isopropyl alcohol, and diethyl ether sequentially to obtain an exemplary compound A-18 (29 mg, yield 25%). The structure of this compound was confirmed by NMR measurement.

$^1$H-NMR (DMSO-$d_6$) δ (ppm): 10.67 (s, 1H), 10.03 (s, 1H), 9.59 (d, 1H), 9.30 (dd, 2H), 9.26 (d, 1H), 9.21 (d, 1H), 9.10-9.03 (m, 3H), 8.88 (d, 1H), 8.49 (d, 1H), 8.17 (d, 1H), 7.99 (t, 1H), 7.93 (d, 1H), 7.87 (t, 1H), 1.97 (s, 6H).

Example 16

Synthesis of Exemplary Compound A-25

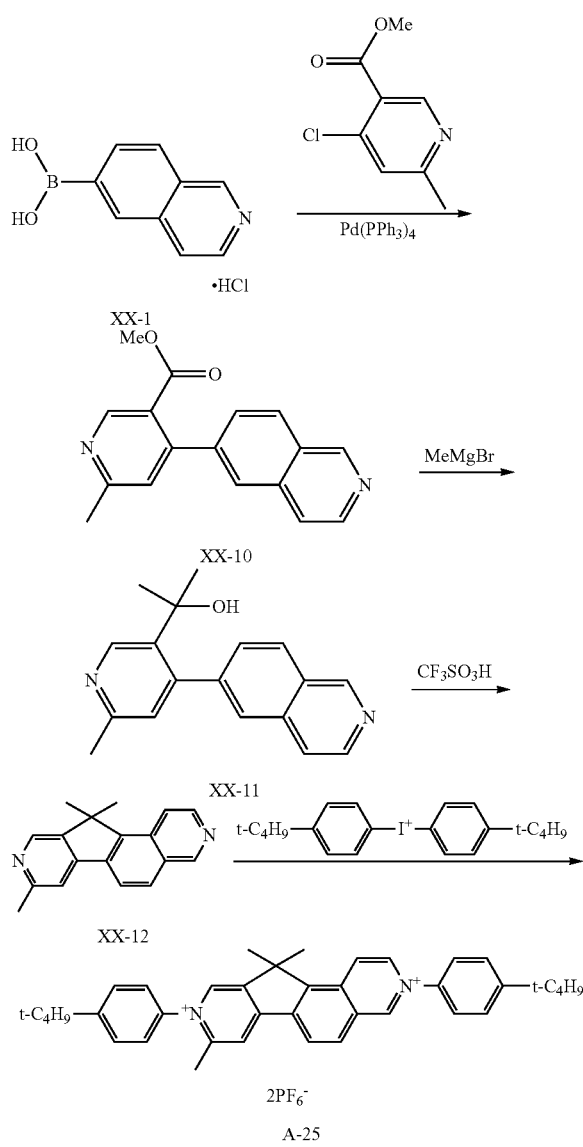

(1) Synthesis of XX-10

In a 100 ml reactor, the XX-1: 790 mg (3.77 mmol) synthesized in Example 1 and methyl 6-methyl-4-chloro-pyridin-3-carboxylate: 636 mg (3.43 mmol) were mixed in 1,4-dioxane (20 ml), and dissolved oxygen was removed with nitrogen. Next, palladium acetate: 38 mg (0.172 mmol), 2-dicyclohexylphosphino-2',6'-dimethoxybiphenyl (S-Phos): 169 mg (0.412 mmol), and potassium carbonate: 1.42 g (10.3 mmol) were added under a nitrogen atmosphere, and the mixture was reacted at 100 degrees Celsius for 6 hours. After water was added to the reaction solution to stop the reaction, the aqueous layer was extracted with ethyl acetate and separated and purified by silica gel chromatography (mobile phase: hexane/ethyl acetate) to obtain an intermediate XX-10 (450 mg, yield 47%).

(2) Synthesis of XX-11

In a 100 ml reactor, the XX-10: 390 mg (1.40 mmol) was mixed in anhydrous tetrahydrofuran (18 ml), and the mixture was cooled to −5 degrees Celsius. Next, methylmagnesium bromide solution: 3.7 ml (approximately 3.0 M of tetrahydrofuran solution, 11 mmol) was slowly put in the reactor in drops, and the mixture was stirred for 3 hours and then elevated to room temperature. After water was added to this solution to stop the reaction, the aqueous layer was extracted with ethyl acetate and separated and purified by silica gel chromatography (mobile phase: chloroform/methanol) to obtain an intermediate XX-11 (355 mg, yield 91%).

(3) Synthesis of XX-12

In a 50 ml reaction container, the XX-11 (350 mg, 1.26 mmol) and trifluoromethanesulfonic acid (3.5 mL) were mixed, and the mixture was stirred at room temperature for 20 hours. After this solution was neutralized with a sodium hydroxide aqueous solution, the aqueous layer was extracted with ethyl acetate and separated and purified by silica gel chromatography (mobile phase: chloroform/methanol) to obtain an intermediate XX-12 (220 mg, yield 67%).

(4) Synthesis of A-25

In a reaction container, the XX-12 (205 mg, 0.79 mmol), bis (4-tert-butylphenyl) iodonium hexafluorophosphate (2.12 g, 3.94 mmol), copper (II) acetate monohydrate (26 mg, 0.14 mmol), and N,N-dimethylformamide (4 mL) were added, and the mixture was reacted at 100 degrees Celsius for 30 hours. After the reaction was completed, the mixture was concentrated under reduced pressure, and an acetonitrile solution (15 ml) of tetrabutylammonium bromide (4 g) was added. The precipitated solid was collected by filtration and dissolved in 10 ml of water. In this solution, an aqueous solution in which 450 mg of ammonium hexafluorophosphate was dissolved was put in drops, and the mixture was stirred at room temperature for 3 hours. The precipitated crystals were filtered and washed with water, isopropyl alcohol, and diethyl ether sequentially to obtain 110 mg of an exemplary compound A-25 (yield: 14%). The structure of this compound was confirmed by NMR measurement.

$^1$H-NMR (DMSO-$d_6$) δ (ppm): 10.57 (s, 1H), 9.70 (s, 1H), 9.19 (d, 1H), 9.14 (d, 1H), 9.06 (s, 1H), 8.93 (d, 1H), 8.85 (d, 1H), 7.95 (d, 2H), 7.86 (d, 2H), 7.82 (d, 2H), 7.72 (d, 2H), 2.64 (s, 3H), 1.94 (s, 6H), 1.41 (s, 9H), 1.40 (s, 9H).

Example 17

Synthesis of Exemplary Compound B-19

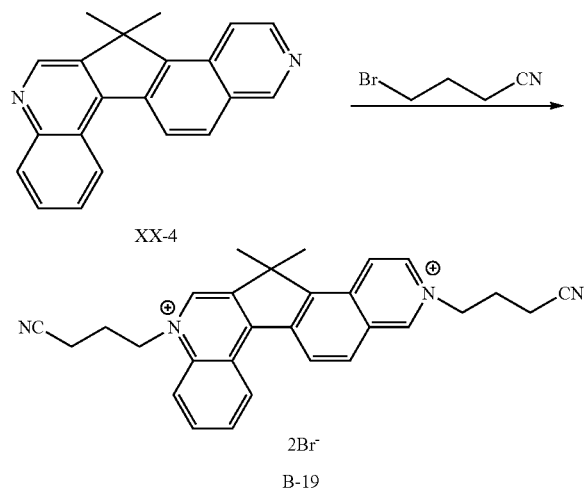

In a reaction container, the XX-4 (292 mg, 0.98 mmol) synthesized in Example 1, 4-bromobutyronitrile (1.45 g, 9.8 mmol) and 3 mL of N,N-dimethylformamide were added, and the mixture was heated and refluxed at 100 degrees Celsius and reacted for 30 hours. After the reaction was completed, ethyl acetate was added and the precipitated crystals were filtered to obtain an exemplary compound B-19 (550 mg, yield 95%). The structure of this compound was confirmed by NMR measurement.

$^1$H-NMR (DMSO-$d_6$) δ (ppm): 10.40 (s, 1H), 10.38 (s, 1H), 9.51 (d, 2H), 9.18 (d, 1H), 9.03 (d, 1H), 8.83 (d, 2H), 8.40 (t, 1H), 8.26 (t, 1H), 5.28 (t, 2H), 4.91 (t, 2H), 2.86 (t, 2H), 2.78 (t, 2H), 2.58-2.40 (m, 4H), 1.98 (s, 6H).

Example 18

Synthesis of Exemplary Compound B-20

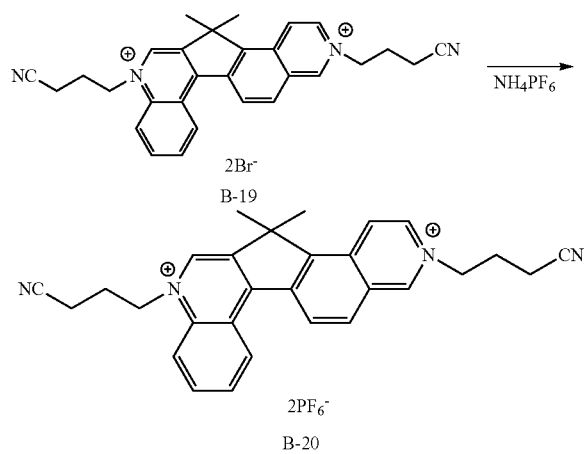

The exemplary compound B-19 (530 mg, 0.89 mmol) synthesized in Example 17 was dissolved in water. An aqueous solution in which 900 mg of ammonium hexafluorophosphate was dissolved was put in drops, and the mixture was stirred at room temperature for 3 hours. The precipitated crystals were filtered and washed with water, isopropyl alcohol, and diethyl ether sequentially to obtain an exemplary compound B-20 (580 mg, yield: 90%). The structure of this compound was confirmed by NMR measurement.

$^1$H-NMR (DMSO-$d_6$) δ (ppm): 10.33 (s, 1H), 10.22 (s, 1H), 9.49 (t, 2H), 9.16 (d, 1H), 9.00 (d, 1H), 8.81 (d, 2H), 8.40 (t, 1H), 8.26 (t, 1H), 5.24 (t, 2H), 4.89 (t, 2H), 2.82 (t, 2H), 2.76 (t, 2H), 2.53-2.40 (m, 4H), 1.96 (s, 6H).

Example 19

Synthesis of Exemplary Compound B-37

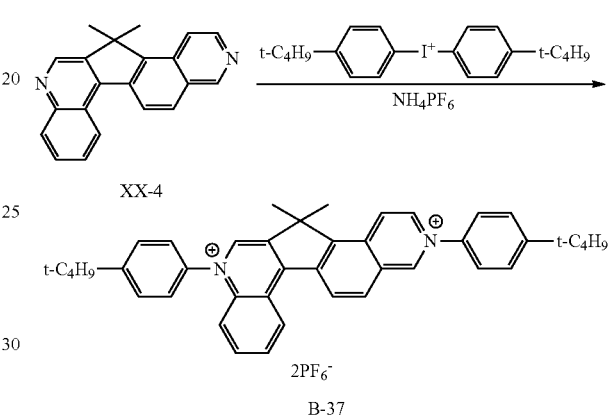

In a reaction container, the XX-4 (173 mg, 0.58 mmol) synthesized in Example 1, bis (4-tert-butylphenyl) iodonium hexafluorophosphate (1.57 g, 2.92 mmol), copper (II) acetate monohydrate (19 mg, 0.10 mmol), and N,N-dimethylformamide (2 mL) were added, and the mixture was reacted at 100 degrees Celsius for 30 hours. After the reaction was completed, the mixture was concentrated under reduced pressure, and an acetonitrile solution (10 ml) of tetrabutylammonium bromide (3 g) was added. The precipitated solid was collected by filtration and dissolved in 50 ml of water. In this solution, an aqueous solution in which 550 mg of ammonium hexafluorophosphate was dissolved was put in drops, and the mixture was stirred at room temperature for 3 hours. The precipitated crystals were filtered and washed with water, isopropyl alcohol, and diethyl ether sequentially to obtain 440 mg of an exemplary compound B-37 (yield: 88%). The structure of this compound was confirmed by NMR measurement.

$^1$H-NMR (DMSO-$d_6$) δ (ppm): 10.63 (s, 1H), 10.33 (s, 1H), 9.63 (d, 1H), 9.56 (t, 1H), 9.22 (d, 2H), 8.95 (d, 1H), 8.28 (d, 2H), 7.99 (d, 2H), 7.91 (d, 2H), 7.89-7.81 (m, 5H), 2.02 (s, 6H), 1.45 (s, 9H), 1.41 (s, 9H).

Examples 20 to 23

An EC element using a compound indicated in Table 2 instead of the exemplary compound B-5 as a cathodic EC compound was manufactured in the same manner as in Example 11, and a high-temperature drive durability test was performed in the same manner as in Example 11. The results of the spectrum change before and after the test are indicated in Table 2.

TABLE 2

|  | Compound | Average transmittance change at decoloring | Maximum value of ΔOD change at coloring |
|---|---|---|---|
| Example 20 | Exemplary compound A-18 | −1.9% | −3.3% |
| Example 21 | Exemplary compound A-25 | −1.1% | −2.2% |
| Example 22 | Exemplary compound B-20 | −0.8% | −1.6% |
| Example 23 | Exemplary compound B-37 | −0.6% | −1.4% |

According to the present disclosure, an organic compound whose absorption peak at coloring ranges from 450 nm to 580 nm and that is superior in high-temperature drive durability can be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-228157, filed Dec. 18, 2019, and Japanese Patent Application No. 2020-124961, filed Jul. 22, 2020, which are hereby incorporated by reference herein in their entirety.

What is claimed is:

1. An organic compound expressed by formula [1]:

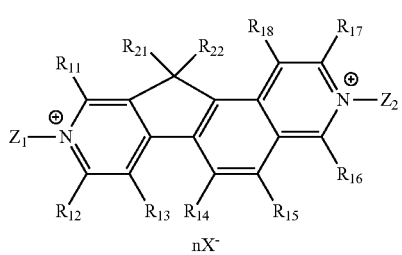

wherein in formula [1], $Z_1$ and $Z_2$ are respectively, independently selected from an alkyl group optionally having a substituent, an aryl group optionally having a substituent, and an aralkyl group optionally having a substituent, $R_{11}$ to $R_{18}$ are respectively, independently selected from a hydrogen atom, an alkyl group optionally having a substituent, an alkoxy group optionally having a substituent, an aryl group optionally having a substituent, a heterocyclic group optionally having a substituent, and a halogen atom, and $R_{12}$ and $R_{13}$ optionally bound to each other to form a ring, $R_{21}$ and $R_{22}$ are respectively, independently selected from a hydrogen atom, a hydroxyl group, an alkyl group optionally having a substituent, an alkoxy group optionally having a substituent, an aryl group optionally having a substituent, and an aralkyl group optionally having a substituent, and $X^-$ represents an anion, n is an integer greater than or equal to 1, and when n is 2 or greater, two or more $X^-$s are the same or different from each other.

2. The organic compound according to claim 1, wherein $R_{12}$ and $R_{13}$ are bound to each other to form a benzene ring.

3. The organic compound according to claim 1, wherein $Z_1$ and $Z_2$ are the same group.

4. The organic compound according to claim 1, wherein $Z_1$ and $Z_2$ are different groups.

5. The organic compound according to claim 1, wherein all of $R_{11}$ to $R_{18}$ are hydrogen atoms.

6. The organic compound according to claim 1, having, in a reduction state, an absorption peak is in a wavelength range from 450 nm to 580 nm.

7. An electrochromic element comprising a pair of electrodes and an electrochromic layer arranged between the pair of electrodes, wherein the electrochromic layer contains the organic compound according to claim 1.

8. The electrochromic element according to claim 7, wherein the electrochromic layer contains a second organic electrochromic compound other than the organic compound.

9. The electrochromic element according to claim 8, wherein the second organic electrochromic compound is an anodic electrochromic compound.

10. The electrochromic element according to claim 8, wherein the electrochromic layer contains a third organic electrochromic compound, and an absorption wavelength region at coloring of the third organic electrochromic compound is different from both the organic compound and the second organic electrochromic compound.

11. The electrochromic element according to claim 10, wherein the second organic electrochromic compound and the third organic electrochromic compound each are a viologen-based compound or a phenazine based compound.

12. The electrochromic element according to claim 7, wherein the electrochromic layer is a solution layer.

13. The electrochromic element according to claim 12, wherein the solution layer has a thickener.

14. The electrochromic element according to claim 13, wherein a mass ratio of the thickener is less than or equal to 20 wt % when a mass of the electrochromic layer is defined as 100 wt %.

15. An optical filter comprising: the electrochromic element according to claim 7; and an active element connected to the electrochromic element.

16. The optical filter according to claim 15, wherein the active element is an active element that drives the electrochromic element and adjusts a light amount of light passing through the electrochromic element.

17. A lens unit comprising: the optical filter according to claim 15; and an imaging optical system having a plurality of lenses.

18. An imaging apparatus comprising: the optical filter according to claim 15; and a light receiving element that receives light that passed through the optical filter.

19. A window member comprising: the electrochromic element according to claim 7; and an active element connected to the electrochromic element.

20. An electrochromic mirror comprising: the electrochromic element according to claim 7; and a light reflection member having the electrochromic element on a light reflection surface.

* * * * *